(12) United States Patent
Sang et al.

(10) Patent No.: US 10,426,441 B2
(45) Date of Patent: Oct. 1, 2019

(54) ULTRASONIC IMAGING SYSTEM AND METHOD FOR EXTRACTING A NONLINEAR SIGNAL COMPONENT

(71) Applicant: Shenzhen Mindray Bio-Medical Electronics Co., Ltd., Shenzhen (CN)

(72) Inventors: Maodong Sang, Shenzhen (CN); Zuhua Mao, Issaquah, WA (US); Tinglan Ji, Sammamish, WA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1000 days.

(21) Appl. No.: 14/444,836

(22) Filed: Jul. 28, 2014

(65) Prior Publication Data

US 2014/0336513 A1    Nov. 13, 2014

Related U.S. Application Data

(63) Continuation-in-part of application No. PCT/CN2012/080925, filed on Sep. 3, 2012.

(30) Foreign Application Priority Data

Dec. 1, 2011    (CN) .......................... 2011 1 0393379

(51) Int. Cl.
*A61B 8/00* (2006.01)
*A61B 8/08* (2006.01)
(Continued)

(52) U.S. Cl.
CPC .......... *A61B 8/5207* (2013.01); *G01S 7/5202* (2013.01); *G01S 7/52034* (2013.01); *G01S 7/52038* (2013.01); *G01S 15/8963* (2013.01)

(58) Field of Classification Search
CPC combination set(s) only.
See application file for complete search history.

(56) References Cited

U.S. PATENT DOCUMENTS 5,905,692 A * 5/1999 Dolazza .............. G01S 7/52023
367/103
6,063,033 A * 5/2000 Haider ................ G01S 7/52034
600/447

(Continued)

FOREIGN PATENT DOCUMENTS

CN          1500445 A       6/2004
CN        101623204 A       1/2010

(Continued)

*Primary Examiner* — James M Kish
(74) *Attorney, Agent, or Firm* — Kory D. Christensen

(57) ABSTRACT

Method and device for performing ultrasonic imaging on a region of interest are disclosed. The method comprises: emitting a first ultrasonic pulse and receiving a first ultrasonic echo signal; emitting a second ultrasonic pulse and receiving a second ultrasonic echo signal; emitting a third ultrasonic pulse and receiving a third ultrasonic echo signal; extracting echo signal components from the first ultrasonic echo signal, the second ultrasonic echo signal and the third ultrasonic echo signal; and producing an ultrasonic image of the region of interest according to the echo signal component; wherein, amplitude weighting of the third ultrasonic pulse is equal to the sum of amplitude weightings of the first ultrasonic pulse and the second ultrasonic pulse in magnitude. The method processes and modulates the plurality of ultrasonic echo signals, so as to separate nonlinear components and linear components in the ultrasonic echo signals.

29 Claims, 14 Drawing Sheets

(51) Int. Cl.
*G01S 7/52* (2006.01)
*G01S 15/89* (2006.01)

(56) References Cited

U.S. PATENT DOCUMENTS

| | | | | |
|---|---|---|---|---|
| 6,074,348 A | * | 6/2000 | Chiao | G01S 7/52039 600/441 |
| 6,186,950 B1 | * | 2/2001 | Averkiou | A61B 8/06 600/440 |
| 6,319,203 B1 | | 11/2001 | Averkiou | |
| 6,454,714 B1 | * | 9/2002 | Ng | A61B 8/06 600/443 |
| 6,458,083 B1 | * | 10/2002 | Jago | A61B 8/08 600/443 |
| 6,558,328 B2 | * | 5/2003 | Chiao | A61B 8/06 600/447 |
| 2001/0016685 A1 | * | 8/2001 | Tsao | G01S 7/52038 600/437 |
| 2005/0124895 A1 | | 6/2005 | Jensen et al. | |
| 2005/0267369 A1 | * | 12/2005 | Lazenby | G10K 11/346 600/447 |
| 2008/0275345 A1 | * | 11/2008 | Bruce | G01S 7/52038 600/458 |
| 2010/0036244 A1 | * | 2/2010 | Angelsen | A61B 8/08 600/438 |
| 2010/0298707 A1 | * | 11/2010 | Fan | A61B 8/08 600/447 |
| 2013/0137986 A1 | * | 5/2013 | Takeda | A61B 8/145 600/447 |

FOREIGN PATENT DOCUMENTS

| | | |
|---|---|---|
| CN | 101677804 A | 3/2010 |
| CN | 101897597 A | 12/2010 |

\* cited by examiner

ULTRASONIC IMAGING SYSTEM AND METHOD FOR EXTRACTING A NONLINEAR SIGNAL COMPONENT

CROSS-REFERENCE TO RELATED APPLICATIONS

This application claims the benefit of Chinese Patent Application No. 201110393379.3, filed on Dec. 1, 2011, which is incorporated herein by reference.

TECHNICAL FIELD

The disclosure relates to medical ultrasound imaging, in particular to methods and devices for ultrasound imaging a region of interest.

BACKGROUND

In a medical ultrasound imaging system, ultrasound pulses are usually transmitted into a body using a transmitting circuit. The ultrasound waves are reflected by interfaces of tissue within the body. Visible ultrasound images of the tissue within the body may be obtained by receiving and processing echoes which carry characteristic information about the tissue within the body.

During ultrasound imaging, weak boundaries and small vessels sometimes may be vaguely imaged or may not be imaged at all because of reverberation and the limitation of resolution. During contrast imaging, there may be a big difference between acoustic impedances of a contrast agent and the surrounding tissues, which may change absorption, reflection, scattering and refraction of acoustic waves within the tissues, thereby enhancing echo signals and improving contrast resolution. In addition, microbubbles of the contrast agent have significant nonlinear characteristics. When being excited by ultrasound pulses, the degrees of stretch and expansion of the microbubbles are different, such that the ultrasound echoes reflected by them contain not only linear components corresponding to the original ultrasound pulses, but also nonlinear components. In the ultrasound echoes reflected by body tissues containing the contrast agent, the linear components contain not only the linear components from the tissue, but also the linear components from the contrast agent. Ultrasound images obtained by detecting and processing fundamental linear components have low contrast resolution and cannot clearly present perfusion of the contrast agent in microangium and tissues, which may affect clinical diagnosis. Therefore, detecting the nonlinear components in the ultrasound echoes during ultrasound contrast imaging may be necessary.

SUMMARY

The present disclosure provides methods and devices which may separate linear components and nonlinear components in ultrasound echo signals very well and conveniently extract the nonlinear components from the ultrasound echo signals.

In some embodiments, a method for ultrasound imaging is provided that may comprise: transmitting a first ultrasound pulse to a region of interest; receiving ultrasound echoes of the first ultrasound pulse reflected from the region of interest to obtain a first ultrasound echo signal; transmitting a second ultrasound pulse to the region of interest; receiving ultrasound echoes of the second ultrasound pulse reflected from the region of interest to obtain a second ultrasound echo signal; transmitting a third ultrasound pulse to the region of interest; receiving ultrasound echoes of the third ultrasound pulse reflected from the region of interest to obtain a third ultrasound echo signal; extracting an echo signal component based on the first ultrasound echo signal, the second ultrasound echo signal and the third ultrasound echo signal; generating an ultrasound image of the region of interest based on the echo signal component; where amplitude weighting of the third ultrasound pulse is equal in magnitude to a sum of amplitude weightings of the first ultrasound pulse and the second ultrasound pulse.

Also, in some embodiments, a device for ultrasound imaging is provided that may comprise: a probe; a transmitting circuit configured to transmit a first ultrasound pulse, a second ultrasound pulse and a third ultrasound pulse to a region of interest through the probe; a receiving circuit configured to, through the probe, respectively receive ultrasound echoes of the first ultrasound pulse to obtain a first ultrasound echo signal, receive ultrasound echoes of the second ultrasound pulse to obtain a second ultrasound echo signal, and receive ultrasound echoes of the third ultrasound pulse to obtain a third ultrasound echo signal; a signal processing module configured to extract an echo signal component based on the first ultrasound echo signal, the second ultrasound echo signal and the third ultrasound echo signal; an image processing module configured to generate an image of the region of interest based on the echo signal component; where amplitude weighting of the third ultrasound pulse is equal in magnitude to a sum of amplitude weightings of the first ultrasound pulse and the second ultrasound pulse.

According to embodiments of the present disclosure, echoes of a plurality of ultrasound pulses with different amplitudes and phases (or polarities) may be processed and the echo signals may be modulated, whereby in the modulated signals, the linear components and the symmetric components of the odd-order nonlinear fundamental components are shifted away from their original frequency positions, while the even-order nonlinear components (for example, the secondary nonlinear components) and the asymmetrical components of the odd-order nonlinear components, particularly the nonlinear fundamental components generated by three-order or higher odd-order components in echoes from contrast agents, still remain at their original frequency positions. Therefore, the separation of the even-order nonlinear components and the asymmetrical components of the odd-order nonlinear components from the linear components and the symmetrical components of the odd-order nonlinear components may be achieved without transmitting the plurality of ultrasound pulses such that the transmissions are delayed with respect to each other, and the even-order nonlinear components and/or the asymmetrical components of the odd-order nonlinear components may be easily extracted from the ultrasound echo signals for subsequent imaging processes, such as contrast agent imaging. Furthermore, according to the embodiments of the present disclosure, the linear components and the symmetrical components of the odd-order nonlinear components may be separated from the even-order nonlinear components and the asymmetrical components of the odd-order nonlinear components without transmitting the plurality of ultrasound pulses such that the transmissions are delayed with respect to each other, therefore the control processes for controlling the plurality of ultrasound pulses to be transmitted such that transmission delays may be avoided.

DETAILED DESCRIPTION

Figure 1:
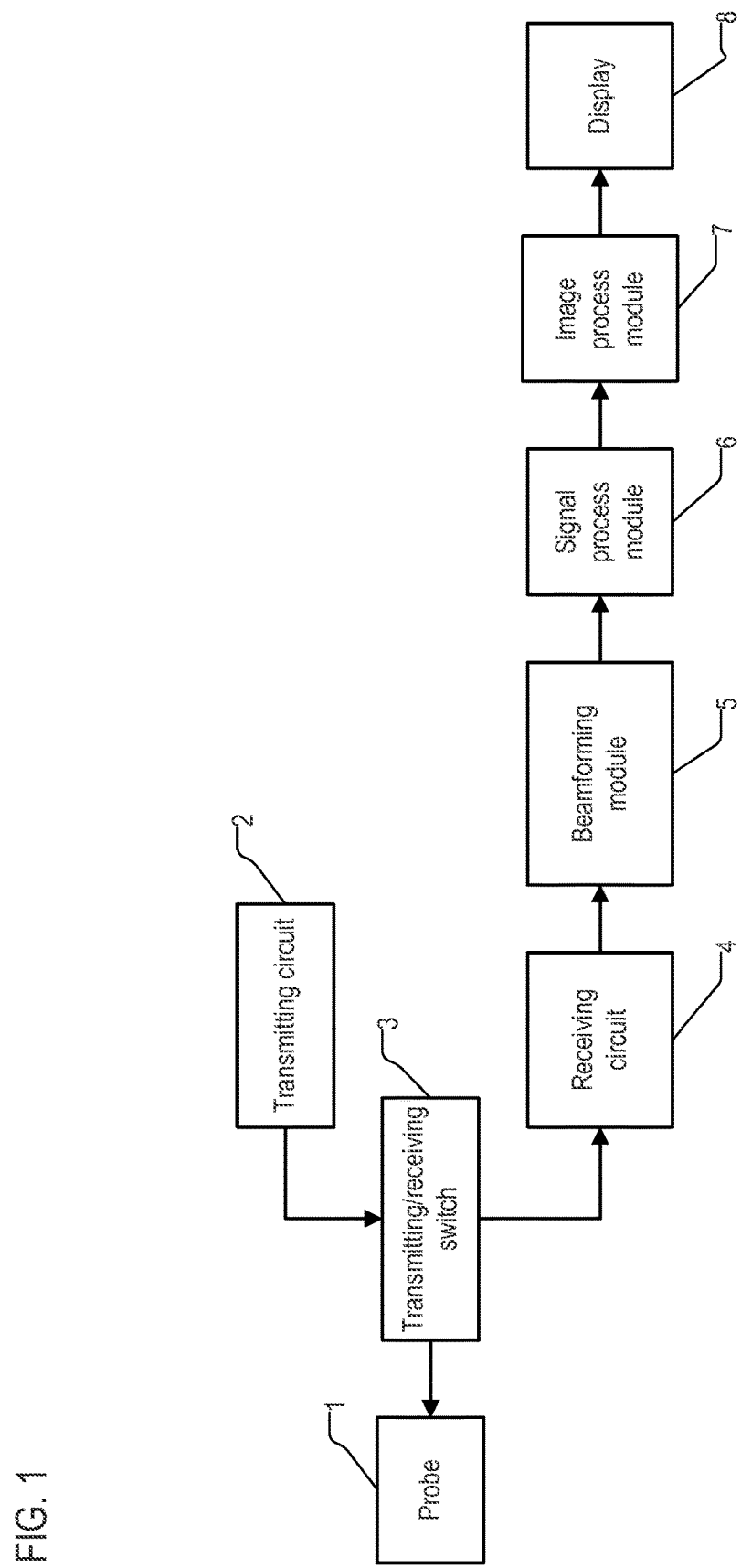
FIG. 1 is a block diagram of a device for ultrasound imaging a region of interest according to an embodiment of the present disclosure.

As shown in FIG. 1, a device for ultrasound imaging of a region of interest according to an embodiment of the present disclosure may include: a probe 1, a transmitting circuit 2, a transmitting/receiving switch 3, a receiving circuit 4, beamforming module 5, signal processing module 6, image processing module 7 and display 8.

The transmitting circuit 2 may transmit exciting pulses which have been delayed for focus and have a certain amplitude and polarity to the probe 1 through the transmitting/receiving switch 3. The probe 1 may be excited by the exciting pulses to transmit ultrasound waves to a region of interest within a body tissue being examined (not shown in the figure), and then, after a certain delay, it may receive ultrasound echoes reflected from the region of interest which contains information about the tissue and converts the ultrasound waves into electrical signals. The receiving circuit 4 may receive the electrical signals converted by the probe 1 to obtain ultrasound echo signals, and send the ultrasound echo signals to the beamforming module 5. The beamforming module 5 may perform a delay for focus, weighting and channel summation, etc. on the ultrasound echo signals and then send the ultrasound echo signals to the signal processing module 6 to undergo related signal processes.

The ultrasound echo signals processed by the signal processing module 6 may be sent to the image processing module 7. Depending on different imaging modes required by the user, the image processing module 7 may perform different processes on the signals to obtain image data under different modes, which then may undergo logarithmic compression, dynamic range adjustment, digital scan conversion and the like to obtain ultrasound images under different modes, such as B mode images, C mode images, D mode images, etc.

The ultrasound images generated by the image processing module 7 may be displayed on the display 8.

Figure 2:
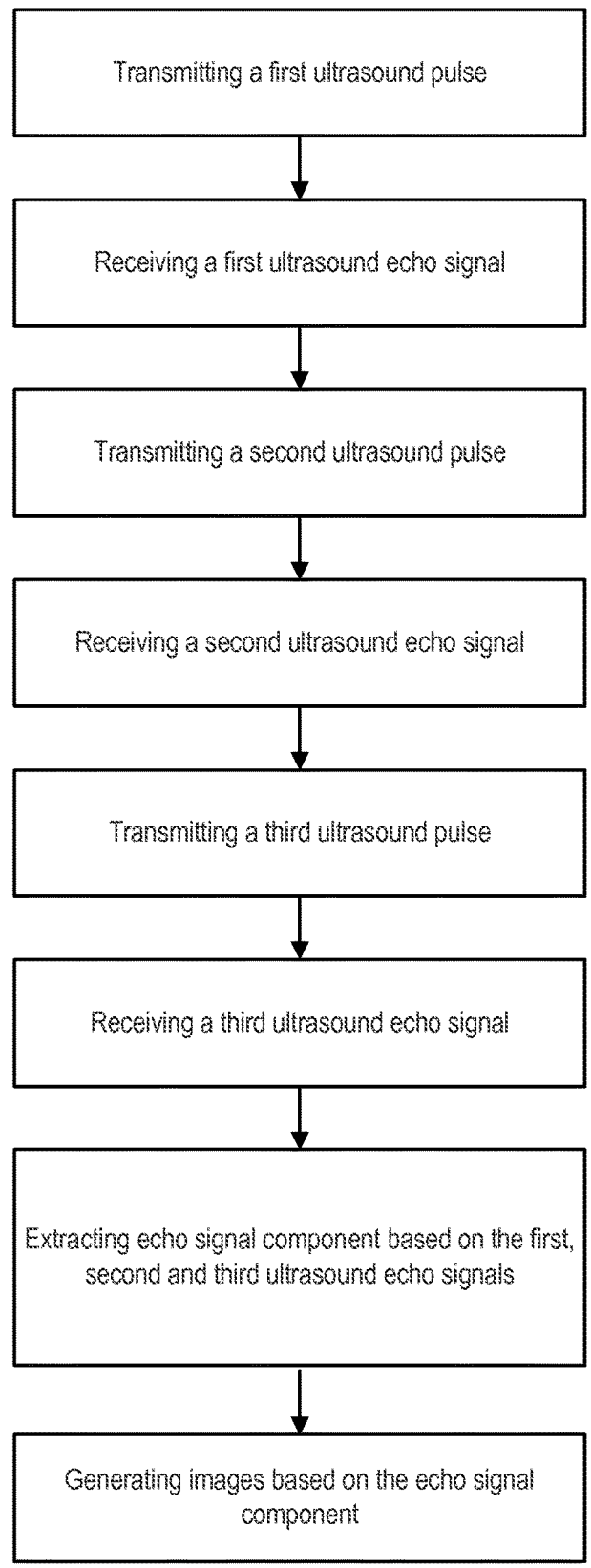
FIG. 2 is a flow chart of a method for ultrasound imaging a region of interest according to an embodiment of the present disclosure.
Figure 3:
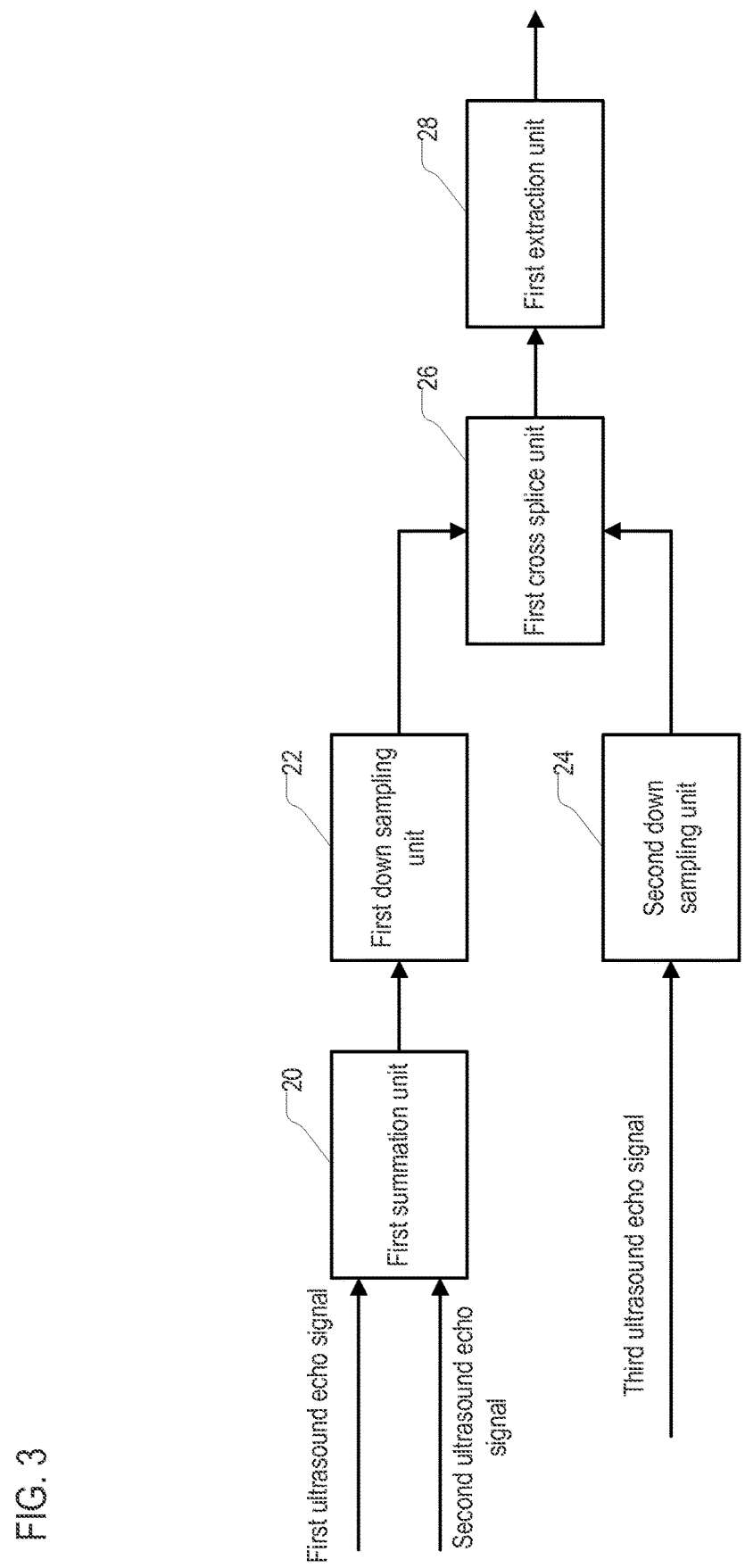
FIG. 3 is a block diagram of a signal process device according to an embodiment of the present disclosure.

According to an embodiment of the present disclosure, a working process of a device for ultrasound imaging of a region of interest is shown in FIG. 2.

The transmitting/receiving switch 3 may be switched into transmitting mode, and the transmitting circuit 2 may transmit a first ultrasound pulse via the probe 1;

The transmitting/receiving switch 3 may be switched into receiving mode, and the receiving circuit 4 may receive ultrasound echoes reflected from the region of interest through the probe 1 to obtain a first ultrasound echo signal;

The transmitting/receiving switch 3 may be switched into transmitting mode, and the transmitting circuit 2 may transmit a second ultrasound pulse via the probe 1;

The transmitting/receiving switch 3 may be switched into receiving mode, and the receiving circuit 4 may receive ultrasound echoes reflected from the region of interest through the probe 1 to obtain a second ultrasound echo signal;

The transmitting/receiving switch 3 may be switched into transmitting mode, and the transmitting circuit 2 may transmit a third ultrasound pulse via the probe 1;

The transmitting/receiving switch 3 may be switched into receiving mode, and the receiving circuit 4 may receive ultrasound echoes reflected from the region of interest through the probe 1 to obtain a third ultrasound echo signal;

Then, the signal processing module 6 may extract the echo signal components needed based on the first ultrasound echo signal, the second ultrasound echo signal and the third ultrasound echo signal obtained (as described in detail below), and the image processing module 7 may generate ultrasound images of the region of interest based on the extracted echo signal components.

During transmitting, the first ultrasound pulse, the second ultrasound pulse and the third ultrasound pulse (which are referred to as transmitted pulses) may have their own respective amplitude and polarity. For example, the kth transmitted pulse may be expressed as:

$$f_k(t) = a_k A(t) \cos(\omega t).$$

Where $A(t)$ represents the envelope of the transmitted pulse, $\cos(\omega t)$ represents the frequency of the carrier wave, and $a_k$ represents the amplitude and polarity of the kth transmitted pulse, where the absolute value of $a_k$ represents the amplitude of the transmitted pulse, and the sign (positive or negative) of $a_k$ represents the polarity of the transmitted pulse.

When transmitting the ultrasound pulses, the transmitting circuit 2 can control the amplitude and the polarity of the transmitted pulse, i.e., control the value of $a_k$. In the present disclosure, $a_k$ is the amplitude weighting of ultrasound pulses, where its absolute value represents the magnitude of the amplitude weighting and its sign represents the direction of the amplitude weighting.

Control of the direction of the amplitude weighting may be achieved by controlling the positive or negative polarity of the transmitted pulses, while control of the magnitude of the amplitude weightings of various transmitted pulses or control of the difference between the magnitudes of amplitude weightings of various transmitted pulses may be achieved in a number of ways. For example:

1. Keeping apertures for various transmitted pulses constant while adjusting exciting voltages of them to cause the absolute value of the amplitude weightings of various exciting voltages to be the same as the absolute value of the amplitude weightings of the transmitted pulses;

2. Keeping the exciting voltages of various transmitted pulses constant while adjusting the number of array elements in transmitting apertures for various pulses. For example, given that the number of the array elements in the transmitting apertures for pulses with a weighting is M and the number of the array elements in the transmitting apertures for pulses with a weighting (1−a) is N, the number of the array elements in the transmitting apertures for pulses with a weighting 1 is (M+N);

3. Making both the exciting voltages and the transmitting apertures of various transmitted pulses different, which may cause the amplitudes of the various transmitted pulses to be different.

In other embodiments, they may also be achieved in other ways and the present disclosure is not limited to these specific ways described above.

The transmitted ultrasound waves may be reflected by tissue medium within the region of interest, and the ultrasound echo signals obtained therefrom may contain both linear fundamental components and high-order nonlinear components. The ultrasound echo signals may be expressed as:

$$y_k(t) = \sum_{i=1} w_i [f_k(t)]^i$$
$$= w_1 a_k A(t)\cos(\omega t) + w_2 a_k^2 A^2(t)\cos^2(\omega t) +$$
$$w_3 a_k^3 A^3(t)\cos^3(\omega t) + \ldots .$$

In the ultrasound echo signals, the component $w_1 a_k A(t) \cos(\omega t)$ may be referred to as a linear fundamental component, the component $w_2 a_k^2 A^2(t)\cos^2(\omega t)$ may be referred to as a secondary nonlinear component, and the component $w_3 a_k^3 A^3(t)\cos^3(\omega t)$ may be referred to as a three-order nonlinear component. In this analogy, they may further contain a four-order nonlinear component, a five-order nonlinear component and other nonlinear components. The nonlinear components mentioned above may be collectively called high-order nonlinear components.

Where $w_i$ is a coefficient of the linear fundamental component or the high-order nonlinear components, wherein i=1, 2, 3 . . . .

Therefore, the amplitude factor of the linear fundamental component of the ultrasound echo signal corresponding to the kth ultrasound pulse may be $w_i a_k$, the amplitude factor of the secondary nonlinear component may be $w_2 a_k^2$, the amplitude factor of the three-order nonlinear component may be $w_3 a_k^3$, and so on.

According to the trigonometric formula:

$$\cos^3(\omega t) = \frac{3}{4}\cos(\omega t) + \frac{1}{4}\cos(3\omega t),$$

in the three-order nonlinear component of the ultrasound echo signals, 75% of the energy is presented in the form of fundamental component $\cos(\omega t)$, which may be referred to as a nonlinear fundamental component; and 25% of the energy is presented in the form of a three-order harmonic component. While in the frequency domain, the three-order harmonic component may be outside of the pass band of the ultrasound probe, and the nonlinear fundamental component may be in the pass band of the probe.

In embodiments of the present disclosure, such nonlinear fundamental components and/or even-order nonlinear components of the ultrasound echo signals may be extracted using the methods and devices according to the present disclosure (as described in detail below).

According to the embodiments, when transmitting the ultrasound pulses, the transmitting circuit 2 may control the amplitude weightings of the first ultrasound pulse, the second ultrasound pulse and the third ultrasound pulse. In one embodiment, the amplitude weightings may be controlled such that the magnitude of the amplitude weighting of the third ultrasound pulse is the same as the magnitude of the sum of the amplitude weightings of the first ultrasound pulse and the second ultrasound pulse.

For example, in one embodiment, the amplitude weighting of the first ultrasound pulse may be a, the amplitude weighting of the second ultrasound pulse may be (1−a), and the amplitude weighting of the third ultrasound pulse may be −1, where 0<a<1; or the amplitude weighting of the first ultrasound pulse may be (1−a), the amplitude weighting of the second ultrasound pulse may be a, and the amplitude weighting of the third ultrasound pulse may be −1, where 0<a<1.

For convenience of description, the disclosure is described herein using normalized amplitude weightings. The concept of normalization is known by those skilled in the art and thus will not be further described herein.

It will be readily understood by those skilled in the art that in the embodiments of the present disclosure, there is no limitation on the sequence for transmitting the first ultrasound pulse, the second ultrasound pulse and the third ultrasound pulse and receiving respective echoes, which may be performed in any sequence. For example, first, the first ultrasound pulse may be transmitted and corresponding echoes may be received, second, the third ultrasound pulse may be transmitted and corresponding echoes may be received, and finally, the second ultrasound pulse may be transmitted and corresponding echoes may be received; or, first, the second ultrasound pulse may be transmitted and corresponding echoes may be received, second, the first ultrasound pulse may be transmitted and corresponding echoes may be received, and finally, the first ultrasound pulse may be transmitted and corresponding echoes may be received; or the like, which will not be listed one by one.

After the first ultrasound echo signal, the second ultrasound echo signal and the third ultrasound echo signal are obtained, the signal processing module 6 may extract needed echo signal components based on the first ultrasound echo signal, the second ultrasound echo signal and the third ultrasound echo signal received. The echo signal components mentioned herein may be asymmetrical components of nonlinear fundamental components and/or even-order nonlinear components in the echo signals.

As mentioned above, the magnitude of the amplitude weighting of the third ultrasound pulse may be the same as the magnitude of the sum of the amplitude weightings of the first ultrasound pulse and the second ultrasound pulse. In addition, the direction of the amplitude weighting of the third ultrasound pulse may be the same as or the reverse of the direction of the sum of the amplitude weightings of the first ultrasound pulse and the second ultrasound pulse.

In one embodiment, the amplitude weighting of the third ultrasound pulse and the sum of the amplitude weightings of the first ultrasound pulse and the second ultrasound pulse may be the same in magnitude and reverse in direction.

A block diagram of the signal processing module 6 is shown in FIG. 2. In this embodiment, the signal processing module may include a first summation unit 20, a first down-sampling unit 22, a second down-sampling unit 24, a first cross-combine unit 26 and a first extraction unit 28.

The first ultrasound echo signal and the second ultrasound echo signal may be input into the first summation unit 20, which may sum the first ultrasound echo signal with the second ultrasound echo signal to obtain a first operation signal. The obtained first operation signal may be sent to the first down-sampling unit 22, which may down-sample the first operation signal to obtain a down-sampled first operation signal.

The third ultrasound echo signal may be sent to the second down-sampling unit 24, which may down-sample the third ultrasound echo signal to obtain a down-sampled third ultrasound echo signal.

Then, the down-sampled first operation signal and the down-sampled third ultrasound echo signal may be input into the first cross-combine/splice unit 26, which may cross-combine the down-sampled first operation signal and the down-sampled third ultrasound echo signal to obtain a second operation signal. The second operation signal may be sent to the first extraction unit 28, which may extract needed echo signal components from the second operation signal, for example, the asymmetrical component of the nonlinear fundamental component or the secondary nonlinear component, which are contained by the ultrasound echo signal.

Hereinafter, some embodiments of the present disclosure will be specifically described with reference to, for example, that the amplitude weighting of the first ultrasound echo is (1−a), the amplitude weighting of the second ultrasound echo is a, and the amplitude weighting of the third ultrasound echo is −1.

Assuming that all of sampling frequencies of the ultrasound echo signals corresponding to the transmitted pulses are Fs. In one embodiment, the process may be as follows:

(1) summing the first ultrasound echo signal and the second ultrasound echo signal to obtain the first operation signal;

First, the first ultrasound echo signal corresponding to the first ultrasound pulse with an amplitude weighting of (1−a) is summed with the second ultrasound echo signal corresponding to the second ultrasound pulse with an amplitude weighting of a. The obtained first operation signal may be expressed as S1(n). Since $$a+(1-a)=1,$$

this signal may contain a linear fundamental component with an amplitude factor of 1.

S1(n) may also contain nonlinear fundamental components generated by the first and second ultrasound pulses with amplitude weightings of (1−a) and a, respectively. The amplitudes of the nonlinear fundamental components may be proportionate to $w_3 \times [a^3+(1-a)^3]$.

Figure 4:
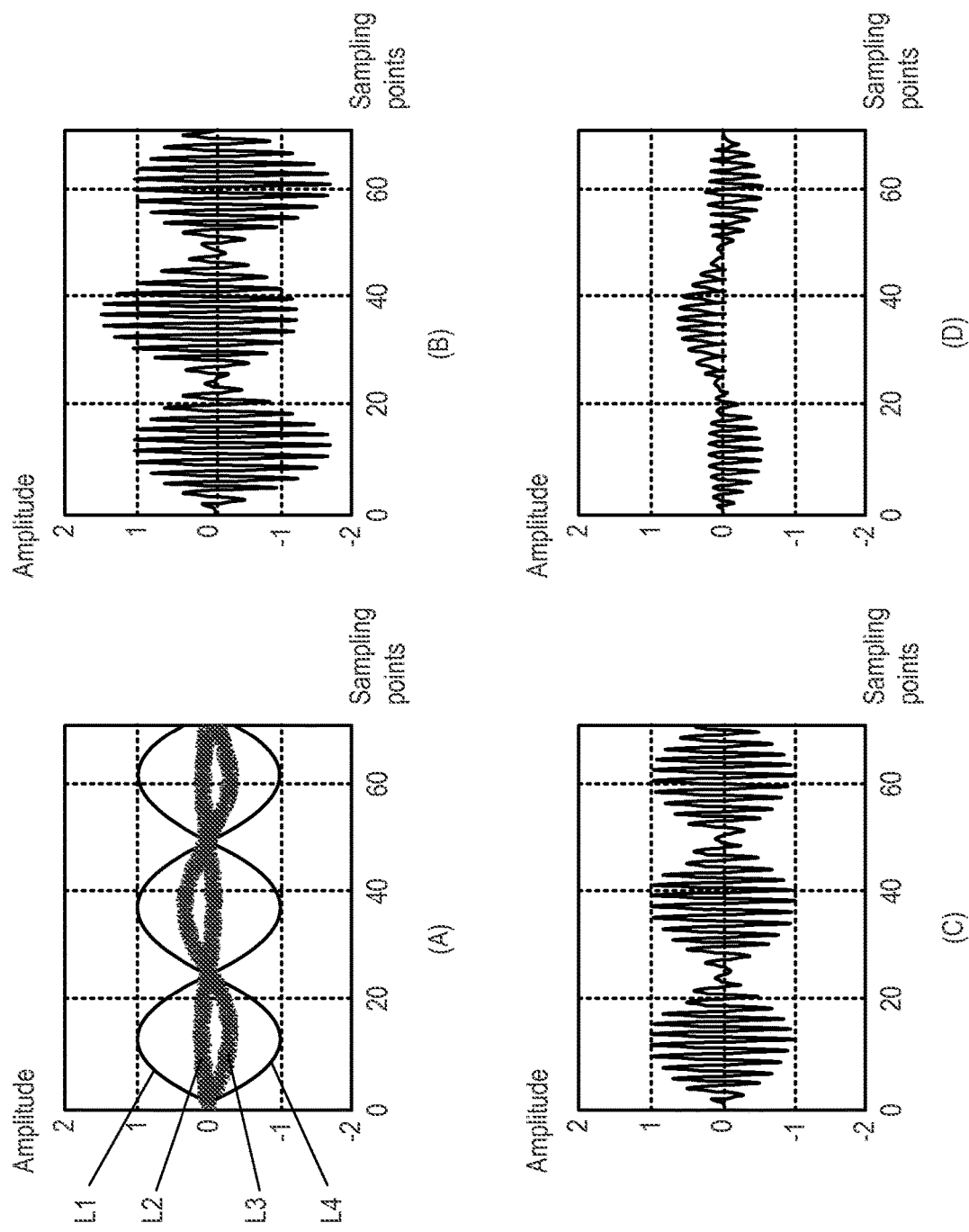
FIG. 4 are schematics showing time domain waveforms of a first operation signal, a third ultrasound echo signal, and a second operation signal as well as an echo signal component thereof according to an embodiment of the present disclosure.

As shown in FIG. 4, the curve L1 in figure (A) is a schematic showing the time domain waveform of the fundamental component of S1(n), and the curve L2 is schematic showing the time domain waveform of the nonlinear fundamental component of S1(n).

(2) down-sampling the first operation signal to obtain the down-sampled first operation signal;

S1(n) may be down-sampled to obtain the down-sampled first operation signal with a sampling frequency of Fs/2. The down-sampled first operation signal obtained by the down-sampling process may be expressed as T1(n).

In one embodiment, the down-sampling process may be performed by selecting data points directly from S1(n) every one data point and serving the selected data points as the data points of T1(n). For example, T1(n) may be:

$$T1(1) = S1(1);$$
$$T1(2) = S1(3);$$
$$\ldots$$
$$T1(n) = S1(2n-1);$$

Where n=1, 2, 3, . . . , N, and N is the length of T1(n), i.e., the total number of data points in T1(n).

Furthermore, in another embodiment, the first down-sampling unit 22 may pre-process S1(n) before down-sampling the same. For example, the first down-sampling unit 22 may sum each data point in S1(n) with at least one adjacent data point and replace the data point with the sum, and then select data points from the pre-processed S1(n) every one data point and serving the selected data points as data points of T1(n). For example, T1(n) may be:

$$T1(1) = S1(1) + S1(2);$$
$$T1(2) = S1(3) + S1(4);$$
$$\ldots$$
$$T1(n) = S1(2n-1) + S1(2n);$$

Where n=1, 2, 3, . . . , N, and N is the length of T1 (n), i.e., the total number of data points in T1(n).

(3) down-sampling the third ultrasound echo signal to obtain a down-sampled third ultrasound echo signal;

The third ultrasound echo signal corresponding to the third ultrasound pulse with an amplitude weighting of −1 may be expressed as S2(n). The third ultrasound echo signal may contain a linear fundamental component with an amplitude factor of −1 and a nonlinear fundamental component which may be proportional to an amplitude factor $w_3 \times (-1)^3 = -w_3$. The curve L4 in FIG. 4 is a schematic showing the time domain waveform of the linear fundamental component of S2(n), and the curve L3 is a schematic showing the time domain waveform of the nonlinear fundamental component of S2(n).

Similarly, the signal S2(n) may be down-sampled to obtain the down-sampled third ultrasound echo signal with a sampling frequency of Fs/2, which is expressed as T2(n).

For example, in one embodiment, the down-sampling process may be performed by selecting data points directly from S2(n) which has been delayed by one data point every one data point and serving the selected data points as the data points of T2(n). For example, T2(n) may be:

$$T2(1) = S2(2);$$
$$T2(2) = S2(4);$$
$$\ldots$$
$$T2(n) = S2(2n);$$

Where n=1, 2, 3, . . . , N, and N is the length of T2(n), i.e., the total number of data points in T2(n).

In another embodiment, the second down-sampling unit 24 may also pre-process S2(n) before down-sampling the same similarly to S1(n). For example, It may be performed by summing each data point in S2(n) with at least one of the adjacent data points and replacing the data point with the sum, and then selecting data points from the pre-processed S2(n), which has been delayed by one data point every one data point and serving the selected data points as data points of T2(n). Thus, T2(n) may be:

$$T2(1) = S2(2) + S2(3);$$
$$T2(2) = S2(4) + S2(5);$$
$$\ldots$$
$$T2(n) = S2(2n) + S2(2n+1);$$

Where n=1, 2, 3, . . . , N, and N is the length of T2(n), i.e., the total number of data points in T2(n).

(4) cross-combining the down-sampled third ultrasound echo signal with the down-sampled first operation signal to obtain a second operation signal;

In the present disclosure, "cross-combining" and "cross-combine" may mean inserting the data points of two signals into each other and combining them to form a new signal. For example, in one embodiment, given that the second operation signal obtained by cross-combining the down-sampled third ultrasound echo signal and the down-sampled first operation signal is expressed as X1(n), X1(n) may be obtained as follows:

$$X1(1) = T1(1);$$
$$X1(2) = T2(1);$$
$$X1(3) = T1(2);$$
$$X1(4) = T2(2);$$
$$\ldots$$
$$X1(2n-1) = T1(n);$$
$$X1(2n) = T2(n);$$

Where n=1, 2, 3, . . . , N, and N is the length of T1(n) or T2(n), i.e., the total number of data points in T1(n) or T2(n).

Therefore, for example, the data points with odd serial numbers in the second operation signal X1(n) obtained by cross-combining may come from the down-sampled first operation signal T1(n), and the data points with even serial numbers may come from the down-sampled third ultrasound echo signal. The schematic showing the time domain waveform of a second operation signal obtained according to one embodiment of the present disclosure is shown in FIG. 4(B).

Although the embodiments above describe them as two signals (for example, T1(n) and T2(n)) cross-combined by inserting the data points of the two signals into each other every one data point, the present disclosure will not be limited thereto. The cross-combining of two signals may also be performed by inserting data points of the two signals into each other in any desired manner to form desired new signals, for example, every two data points, every three data points, or in various ways, etc.

The obtained second operation signal X1(n) may contain both linear fundamental components and nonlinear fundamental components derived from high-order terms. The schematics showing the time domain waveforms of the linear fundamental component and the nonlinear fundamental component in a second operation signal according to one embodiment of the present disclosure are shown in FIGS. 4(C) and 4(D), respectively. The linear fundamental components contained in the second operation signal which derive from S1(n) and S2(n) respectively may have the same amplitudes, but reverse polarity (a phase difference of 180 degrees). In the second operation signal obtained by the cross-combining, the linear fundamental component is modulated from its original frequency position F0 to frequency position Fs/2±F0 by a modulation frequency with a frequency of Fs/2, as shown in FIG. 4(C), and the nonlinear fundamental component, as shown in FIG. 4(D), may be divided into two portions: one is a symmetrical component with an amplitude factor of $a^3+(1-a)^3$, and the other is an asymmetrical component with an amplitude factor of $1-[a^3+(1-a)^3]$. The symmetrical component of the nonlinear fundamental component may exist in both S1(n) and S2(n), while the asymmetrical component may be the difference between the nonlinear fundamental components in S1(n) and S2(n). This difference may be proportional to $1-[a^3+(1-a)^3]$.

Figure 5:
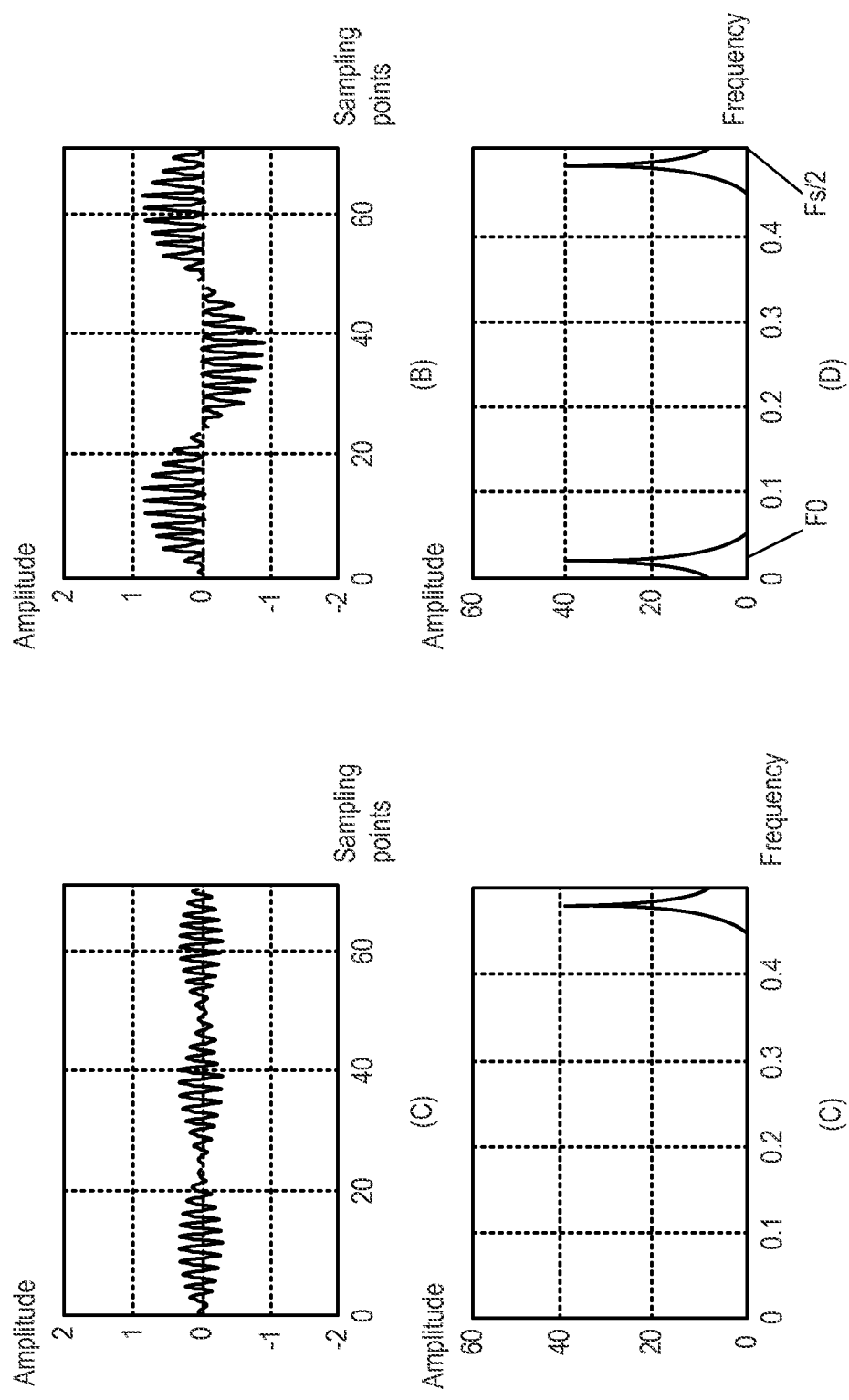
FIG. 5 are schematics showing time domain waveforms and spectrums of a symmetrical component and an asymmetrical component of a nonlinear fundamental component according to an embodiment of the present disclosure.

In FIG. 5, (A) and (B) provide the schematics showing the time domain waveforms of the symmetrical component and the asymmetrical component in the nonlinear fundamental component according to one embodiment of the present disclosure, respectively. FIG. 5(C) and FIG. 5(D) provide their spectrums, respectively. FIG. 5(C) shows that the symmetrical component of the nonlinear fundamental component in the second operation signal generated by S1(n) and S2(n) (T1(n) and T2(n) are obtained by down-sampling S1(n) and S2(n), respectively, therefore the second operation signal may also be considered as being generated by S1(n) and S2(n)) is modulated to both sides of Fs/2, and the asymmetrical component of the nonlinear fundamental component remains at its original frequency position F0.

Therefore, both the linear fundamental component and the symmetrical component of the nonlinear fundamental component of the second operation signal may be modulated to both sides of Fs/2, and the asymmetrical component of the nonlinear fundamental component may remain at its original frequency position F0. In addition, the even-order nonlinear components in the second operation signal remain at their original frequency positions. For example, the secondary nonlinear component remains at its original frequency position 2F0. In fact, in some embodiments of the present disclosure, the linear component and the symmetrical components of odd-order nonlinear fundamental components in an operation signal obtained by cross-combining may be shifted away from their original frequency positions, and the even-order nonlinear components and the asymmetrical components of the odd-order nonlinear fundamental components, particularly the nonlinear fundamental components generated by three-order or higher odd-order components in echoes from contrast agents, still remain at their original frequency positions. In embodiments of the present disclosure, the first ultrasound pulse, the second ultrasound pulse and the third ultrasound pulse need not be transmitted in a way that transmissions are delayed with respect to each other. Therefore, the embodiments of the present disclosure may separate the linear components and the symmetrical components of the odd-order nonlinear fundamental components from the even-order nonlinear components and the asymmetrical components of the odd-order nonlinear fundamental components with each other without the need for transmitting the ultrasound pulses in a way that the transmissions are delayed with respect to each other.

(5) extracting needed signal components from the second operation signal;

As described above, both the linear fundamental component and the symmetrical component of the nonlinear fundamental component in the second operation signal may be modulated to the both sides of Fs/2, i.e., may be modulated to higher frequency positions, while the asymmetrical component of the nonlinear fundamental component and the secondary nonlinear component may remain at their original frequency positions. Therefore, the linear fundamental component and the symmetrical component of the nonlinear fundamental component in the second operation signal may be separated in the frequency domain from the asymmetrical component of the nonlinear fundamental component and the second nonlinear component. Therefore, the needed signal components may be extracted from the second operation signal by the first extraction unit.

Figure 6:
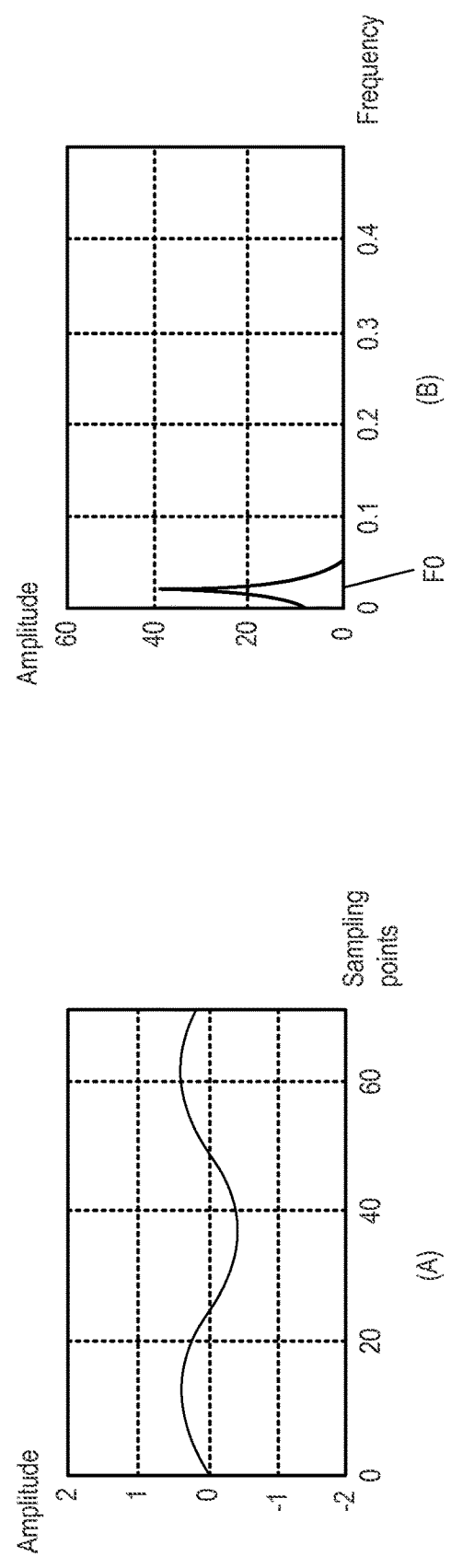
FIG. 6 are schematics showing time domain waveforms and spectrums of a nonlinear fundamental component obtained by low pass filtering and a second operation signal according to an embodiment of the present disclosure.

For example, in one embodiment, the first extraction unit may be a low-pass filter. The signal component extracted from the second operation signal may be the asymmetrical component of the nonlinear fundamental component. For example, after the second operation signal passes through the low-pass filter, the linear fundamental component and the symmetrical component of the nonlinear fundamental component which have been modulated from their original frequency position F0 to (Fs/2)±F0 may be removed by the low-pass filter, while the asymmetrical component of the nonlinear fundamental component may be output. As shown in FIG. 6, (A) and (B) are, respectively, schematics showing the time domain waveform and spectrum of the nonlinear fundamental component output by the low-pass filter after the second operation signal passes through the low-pass filter according to one embodiment of the present disclosure.

Furthermore, in one embodiment of the present disclosure, the even-order nonlinear component, such as the secondary nonlinear component, may also be extracted from the second operation signal by the first extraction unit.

(6) generating images of the region of interest based on the extracted signal component;

After the needed signal components, such as the asymmetrical component of the nonlinear fundamental component and/or the secondary nonlinear component, are extracted, the images of the region of interest may be generated based on these extracted signal components. The methods for generating images of the region of interest based on the signal components may be common methods in the art and will not be described in detail herein.

Figure 7:
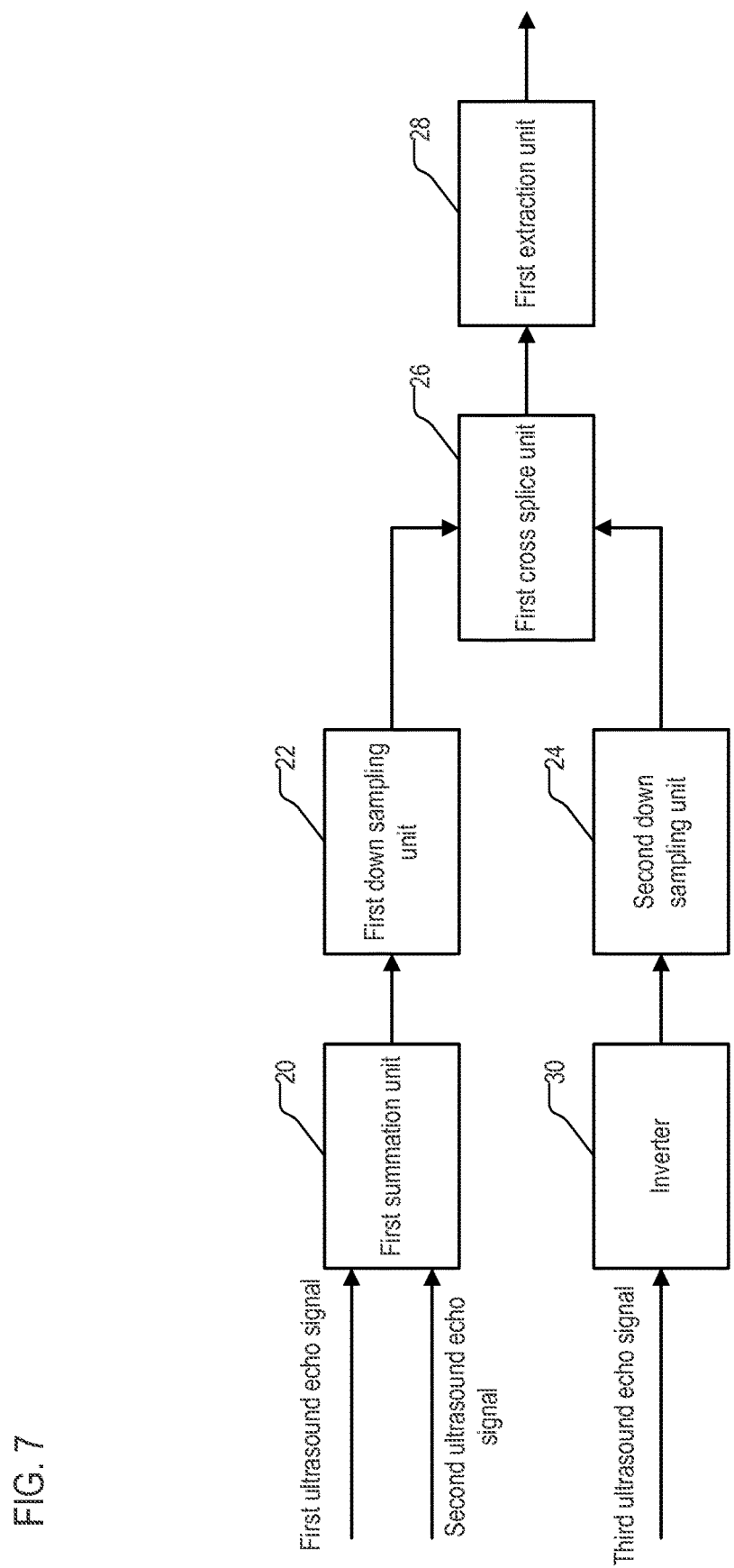
FIG. 7 is a block diagram of a signal process device according to another embodiment of the present disclosure.

In the embodiments described above, the direction of the amplitude weighting of the third ultrasound pulse is reversed to the direction of the sum of the amplitude weightings of the first ultrasound pulse and the second ultrasound pulse. However, in other embodiments, the direction of the amplitude weighting of the third ultrasound pulse may be the same as the direction of the sum of the amplitude weightings of the first ultrasound pulse and the second ultrasound pulse. In this case, before being down-sampled, the third ultrasound echo signal may be inverted. That is, an inverter may be added before the second down-sampling unit 24 in the embodiments described above, as shown in FIG. 7. Other configurations and processing methods in such embodiments may be the same as or similar to those in the embodiments described above and will not be described in detail.

In one embodiment of the present disclosure, the ultrasound imaging process shown in FIG. 2 may further include:

The transmitting/receiving switch 3 may be switched into transmitting mode, and the transmitting circuit 2 may transmit a fourth ultrasound pulse via the probe 1;

The transmitting/receiving switch 3 may be switched into receiving mode, and the receiving circuit 4 may receive ultrasound echoes reflected from the region of interest through the probe 1 to obtain a fourth ultrasound echo signal;

Where the amplitude weighting of the third ultrasound pulse and the sum of the amplitude weightings of the first ultrasound pulse and the second ultrasound pulse may be the same in magnitude and reverse in direction; the amplitude weighting of the fourth ultrasound pulse and the sum of the amplitude weightings of the first ultrasound pulse and the second ultrasound pulse may be the same in magnitude and in direction.

Then, the signal processing module 6 may extract the needed echo signal component based on the first ultrasound echo signal, the second ultrasound echo signal, the third ultrasound echo signal and the fourth ultrasound echo signal received, and the image processing module 7 may generate ultrasound images of the region of interest based on the extracted echo signal component.

Figure 8:
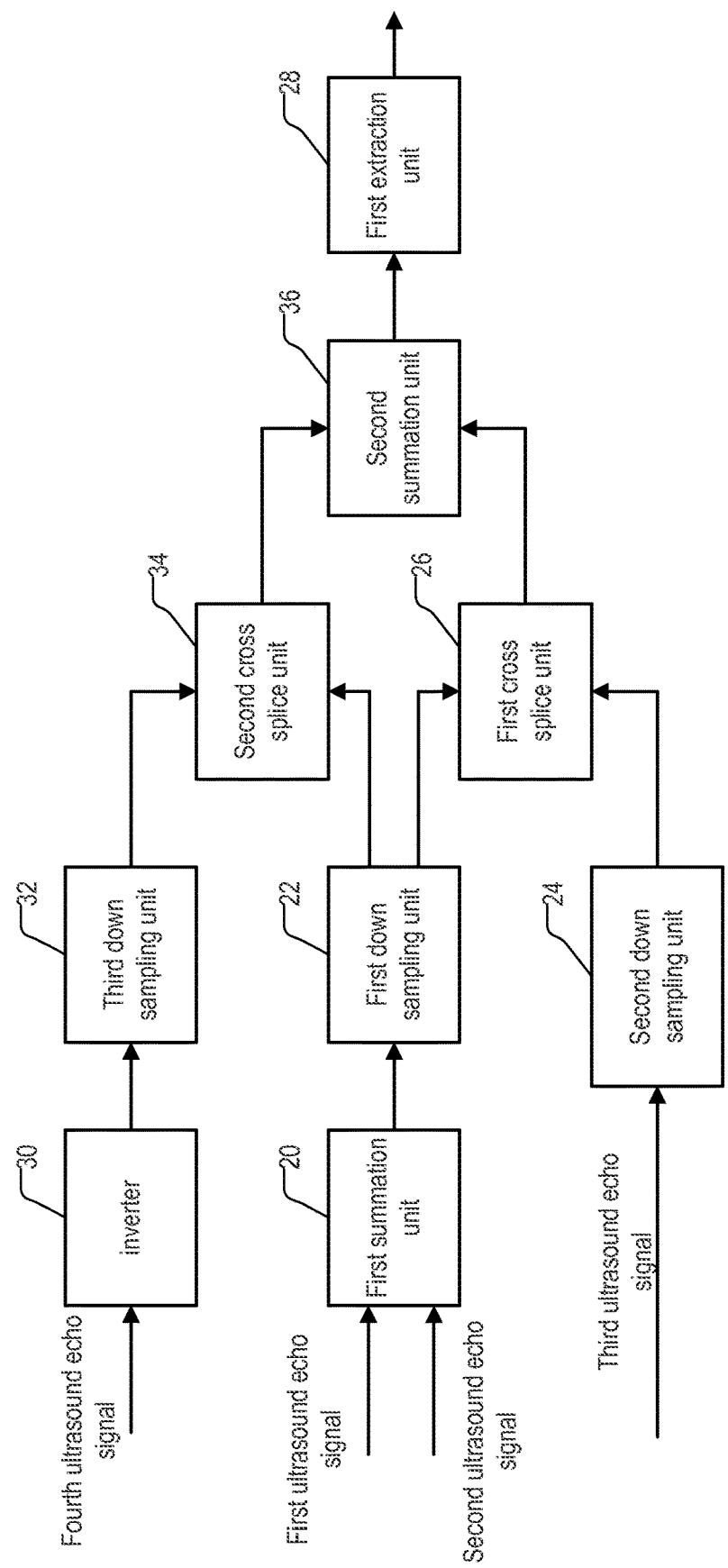
FIG. 8 is a block diagram of a signal process device according to still another embodiment of the present disclosure.

In these embodiments, as shown in FIG. 8, besides the first summation unit 20, the first down-sampling unit 22, the second down-sampling unit 24, the first cross-combine/splice unit 26 and the first extraction unit 28, the signal processing module may further include an inverter 30, a third down-sampling unit 32, a second cross-combine unit 34 and a second summation unit 36.

In these embodiments, the process of the signal processing module 6 may include:

The first ultrasound echo signal and the second ultrasound echo signal may be input into the first summation unit 20. The first summation unit 20 may sum the first ultrasound echo signal and the second ultrasound echo signal to obtain a first operation signal. The obtained first operation signal may be sent to the first down-sampling unit 22. The first down-sampling unit 22 may down-sample the first operation signal to obtain a down-sampled first operation signal;

The third ultrasound echo signal may be input into the second down-sampling unit 24. The second down-sampling unit 24 may down-sample the third ultrasound echo signal to obtain a down-sampled third ultrasound echo signal;

The fourth ultrasound echo signal may be input into the inverter 30. The inverter 30 may invert the fourth ultrasound echo signal to obtain a fourth inverted ultrasound echo signal, which may be input into the third down-sampling unit 32. The third down-sampling unit 32 may down-sample the fourth inverted ultrasound echo signal to obtain a down-sampled, inverted fourth ultrasound echo signal;

Then, the down-sampled first operation signal and the down-sampled third ultrasound echo signal may be input into the first cross-combine unit 26, which may cross-combine the down-sampled first operation signal and the down-sampled third ultrasound echo signal to obtain a second operation signal. The down-sampled first operation signal and the down-sampled, inverted fourth ultrasound echo signal may be input into the second cross-combine unit 34, which may cross-combine the down-sampled first operation signal and the down-sampled, inverted fourth ultrasound echo signal to obtain a third operation signal;

The obtained second operation signal and the third operation signal may be input into the second summation unit 36, which sums the second operation signal and the third operation signal to obtain a fourth operation signal;

The obtained fourth operation signal may be sent to the first extraction unit 28, which may extract needed echo signal components from the fourth operation signal, such as the nonlinear fundamental component or the secondary nonlinear component contained in the ultrasound echo signal.

In such embodiments, the methods for down-sampling the first operation signal, the third ultrasound echo signal and the fourth ultrasound echo signal and the methods for pre-processing the signals before down-sampling the same, the methods for cross-combining the down-sampled first operation signal and the down-sampled, inverted fourth ultrasound echo signal, and the methods for cross-combining the down-sampled first operation signal and the down-sampled third ultrasound echo signal may be the same as or similar to those in the embodiments described above and will not be described in detail again. The method for extracting the needed signal components from the fourth operation signal may be low-pass filtering, and the first extraction unit 28 may be a low-pass filter.

For example, given that the fourth ultrasound echo signal is expressed as S3(n), S3(n) may be inverted to obtain −S3(n). Then, −S3(n) may be processed the same as S2(n). For example, given that the down-sampled, inverted fourth ultrasound echo signal is expressed as T3(n), in one embodiment, it may be performed by selecting data points in −S3(n) which has been delayed by one data point every one data point and serving the selected data points as data points of T3(n). For example, T3(n) may be:

$$T3(1) = -S3(2);$$
$$T3(2) = -S3(4);$$
$$...$$
$$T3(n) = -S3(2n);$$

Where n=1, 2, 3, . . . , N, and N is the length of T3(n), i.e., the total number of data points in T3(n).

Or, in other embodiments, the third down-sampling unit 32 may pre-process −S3(n) before down-sampling the same similarly to S1(n). For example, it may be performed by summing each data point in −S3(n) with at least one of the adjacent data points and replacing the data point with the sum, and then selecting data points in the pre-processed −S3(n) which has been delayed by one data point every one data point and serving the selected data points as data points of T3(n). For example, T3(n) may be:

$$T3(1) = -[S2(2) + S2(3)];$$
$$T3(2) = -[S2(4) + S2(5)];$$
$$...$$
$$T3(n) = -[S2(2n) + S2(2n+1)];$$

Where n=1, 2, 3, . . . , N, and N is the length of T3(n), i.e., the total number of data points in T3(n).

In these embodiments, the linear fundamental components and the symmetrical components of the nonlinear fundamental components in the second operation signals and the third operation signals may be modulated to both sides of Fs/2, i.e., to higher frequency positions, while the asymmetrical components of the nonlinear fundamental components and the secondary nonlinear components may remain at their original frequency positions. The signal components needed may be extracted from the sums of the second operation signals and the third operation signals by the first extraction unit 28. Since there may be correlation between valid signals in the second operation signal and the third operation signal while no correlation between noises in them, extracting the needed signal components from the sums of the second operation signals and the third operation signals may further increase the signal-to-noise ratio of the extracted signal components.

Figure 9:
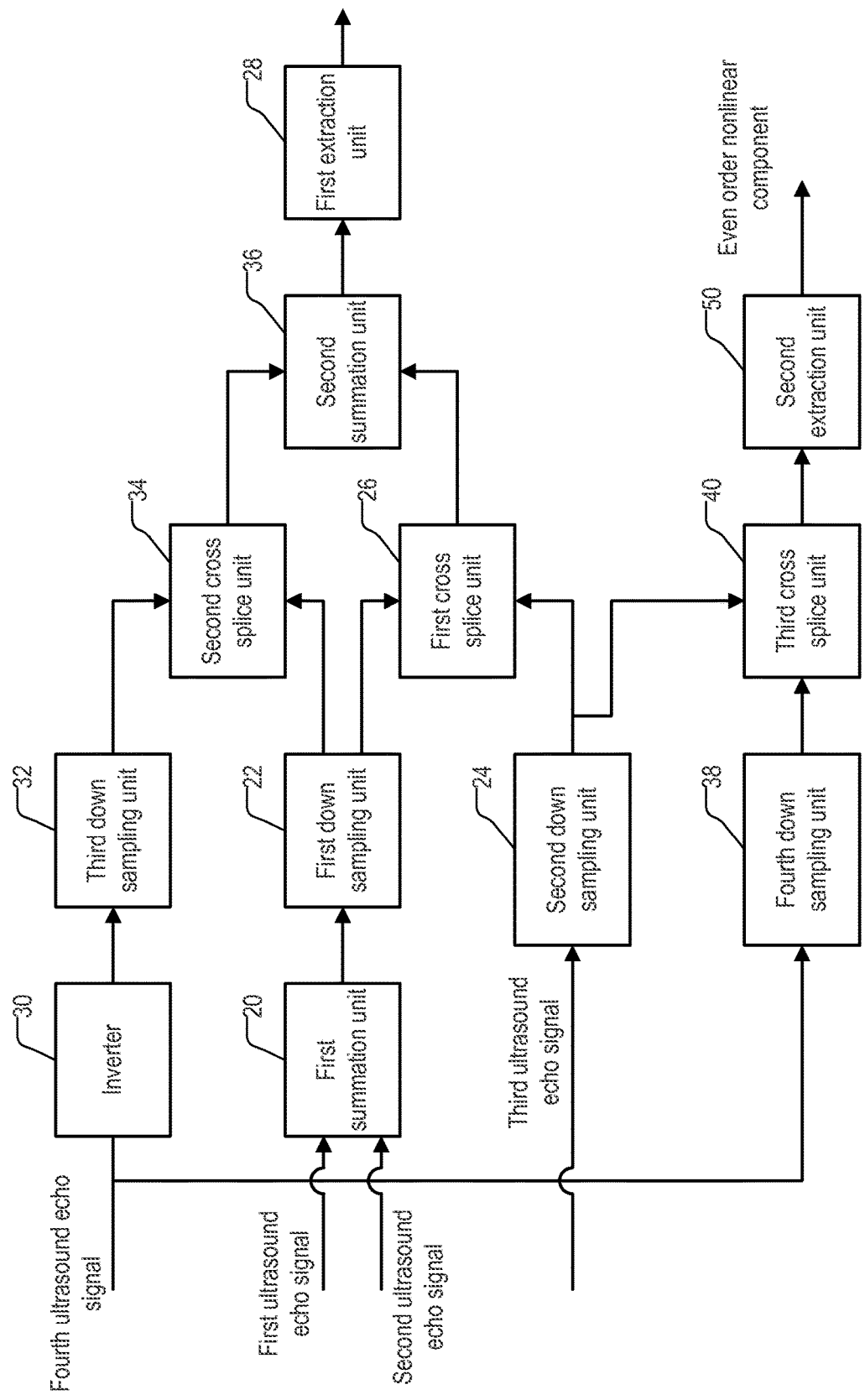
FIG. 9 is a block diagram of a signal process device according to still another embodiment of the present disclosure.

As shown in FIG. 9, in some embodiments of the present disclosure, the embodiment shown in FIG. 8 may further include a fourth down-sampling unit 38, a third cross-combine unit 40 and a second extraction unit 50.

As described above, in one embodiment, the data points of the third ultrasound echo signal S2(n) or the pre-processed third ultrasound echo signal which has been delayed by one data point may be selected every one data point and the selected data points may serve as data points of the down-sampled third ultrasound echo signal T2(n). In such embodiments, the fourth ultrasound echo signal S3(n) may further be processed by the fourth down-sampling unit 38, which may select data points from the fourth ultrasound echo signal S3(n) or from the fourth ultrasound echo signal which has been pre-processed similarly to those described above every one data point, and the selected data points may serve as the data points of the down-sampled fourth ultrasound echo signal T4(n). The specific processes for down-sampling and pre-processing may be the same as or similar to those described above and will not be described in detail.

Then, the down-sampled third ultrasound echo signal T2(n) and the down-sampled fourth ultrasound echo signal T4(n) may be combined in the third cross-combine unit 40. The specific methods and processes for cross-combining may be the same as or similar to those in the embodiments described above and will not be described in detail again. After the cross-combine, a fifth operation signal may be obtained, which may be expressed as X3(n).

Figure 10:
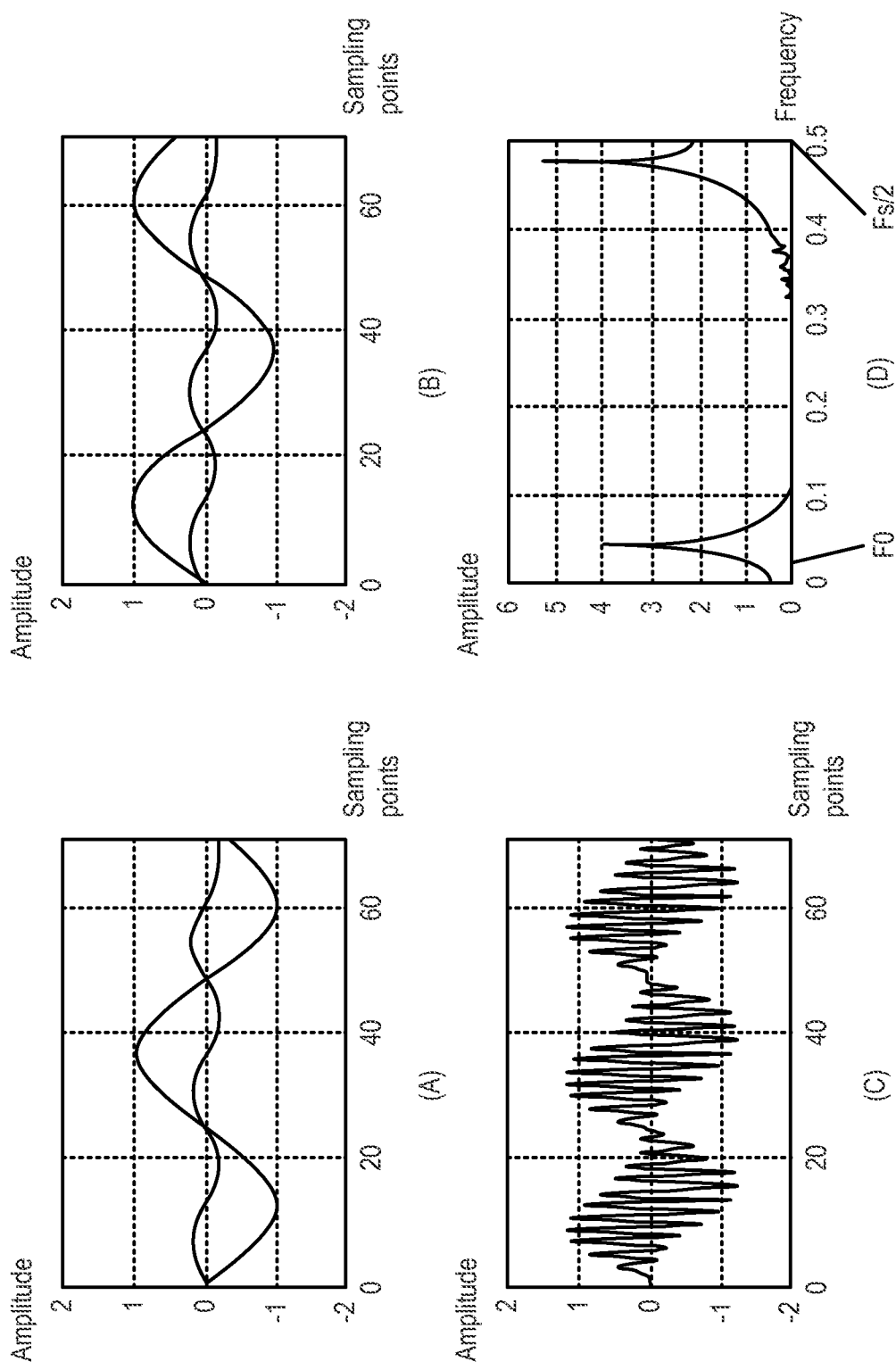
FIG. 10 is a group of schematics showing time domain waveforms and spectrums of a third ultrasound echo signal, a fourth ultrasound echo signal and a fifth operation signal according to an embodiment of the present disclosure.

The fifth operation signal X3(n) may be obtained by cross-combining the down-sampled third ultrasound echo signal S2(n) (the amplitude weighting of which may be, for example, −1) and the down-sampled fourth ultrasound echo signal S3(n) (the amplitude weighting of which may be, for example, 1). S2(n) and S3(n) contain both a fundamental component and a secondary nonlinear component. In FIG. 10, (A) and (B) are the schematics showing the time domain waveforms of the fundamental components and the secondary nonlinear components in S2(n) and S3(n) according to an embodiment of the present disclosure. In this embodiment, the linear fundamental components in S2(n) and S3(n) have the same amplitudes, but reverse polarity (with a phase difference of 180 degrees), while the secondary nonlinear components in them have the same phases.

Figure 11:
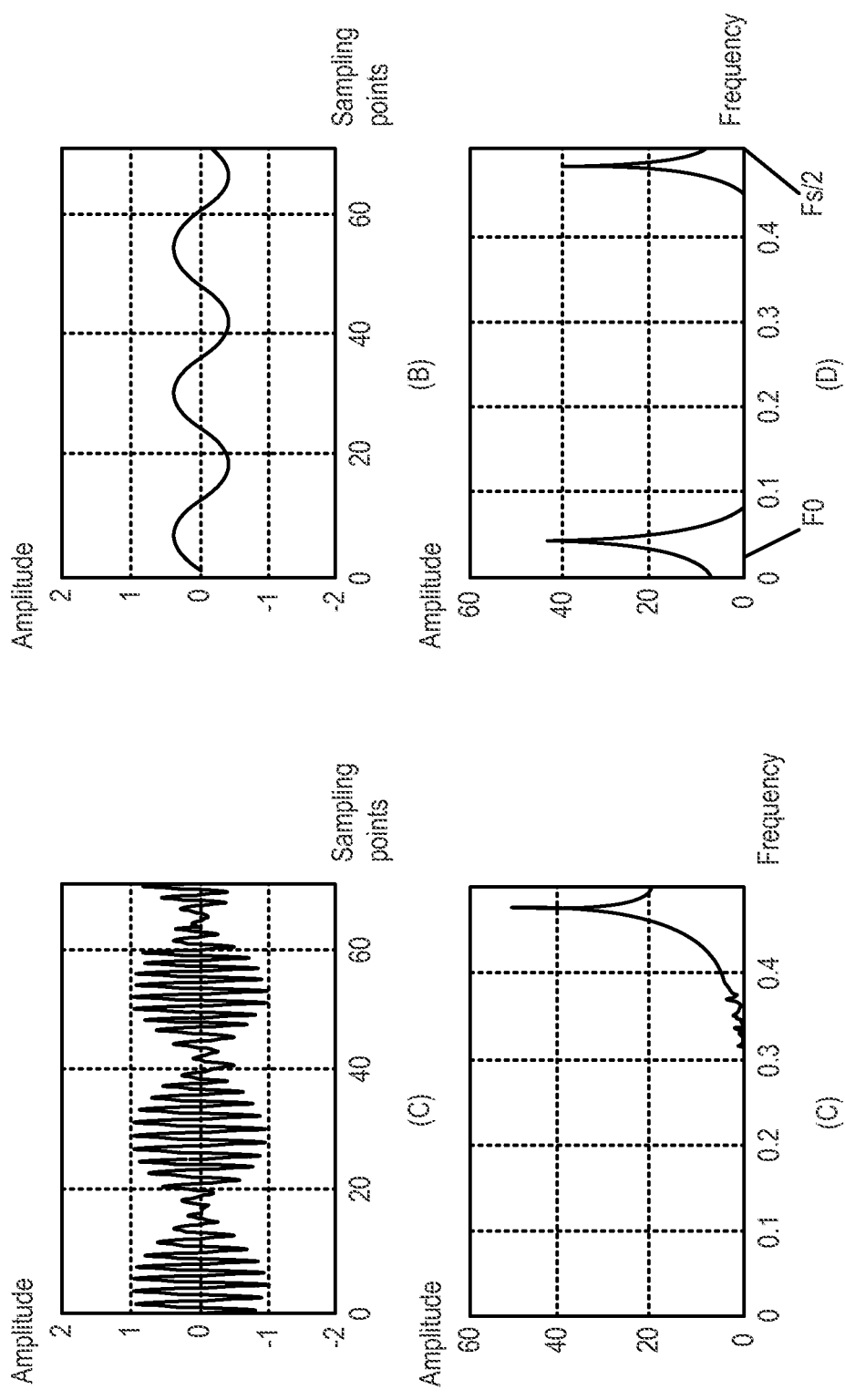
FIG. 11 is a group of schematics showing time domain waveforms and spectrums of linear fundamental components and secondary nonlinear components of a fifth operation signal according to an embodiment of the present disclosure.

As shown in FIG. 10, (C) is a schematic showing the time domain waveform of X3(n) according to an embodiment of the present disclosure, and (D) is a schematic showing the spectrum of X3(n) according to an embodiment of the present disclosure. As shown in FIG. 11, (A) and (C) are schematics showing the time domain waveform and spectrum of the linear fundamental component of X3(n), respectively, and (B) and (D) are schematics showing the time domain waveform and spectrum of the secondary nonlinear component of X3(n), respectively.

FIG. 10(C), (D) and FIG. 11 show that the linear fundamental component in the fifth operation signal X3(n) is modulated from F0 to (Fs/2)±F0, while the secondary nonlinear component remains at its original position 2F0 in frequency domain.

Therefore, the secondary nonlinear component in the fifth operation signal may be extracted by the second extraction unit 50, which may be a low-pass filter.

In these embodiments, the fifth operation signal obtained by cross-combining may be obtained based on the echo signals corresponding to the third ultrasound pulse and the fourth ultrasound pulse with amplitude weightings of −1 and 1 respectively (i.e., the third ultrasound echo signal and the fourth ultrasound echo signal), therefore, the secondary nonlinear component of the fifth operation signal may be enhanced, which may facilitate subsequent extraction of the secondary nonlinear component.

Figure 12:
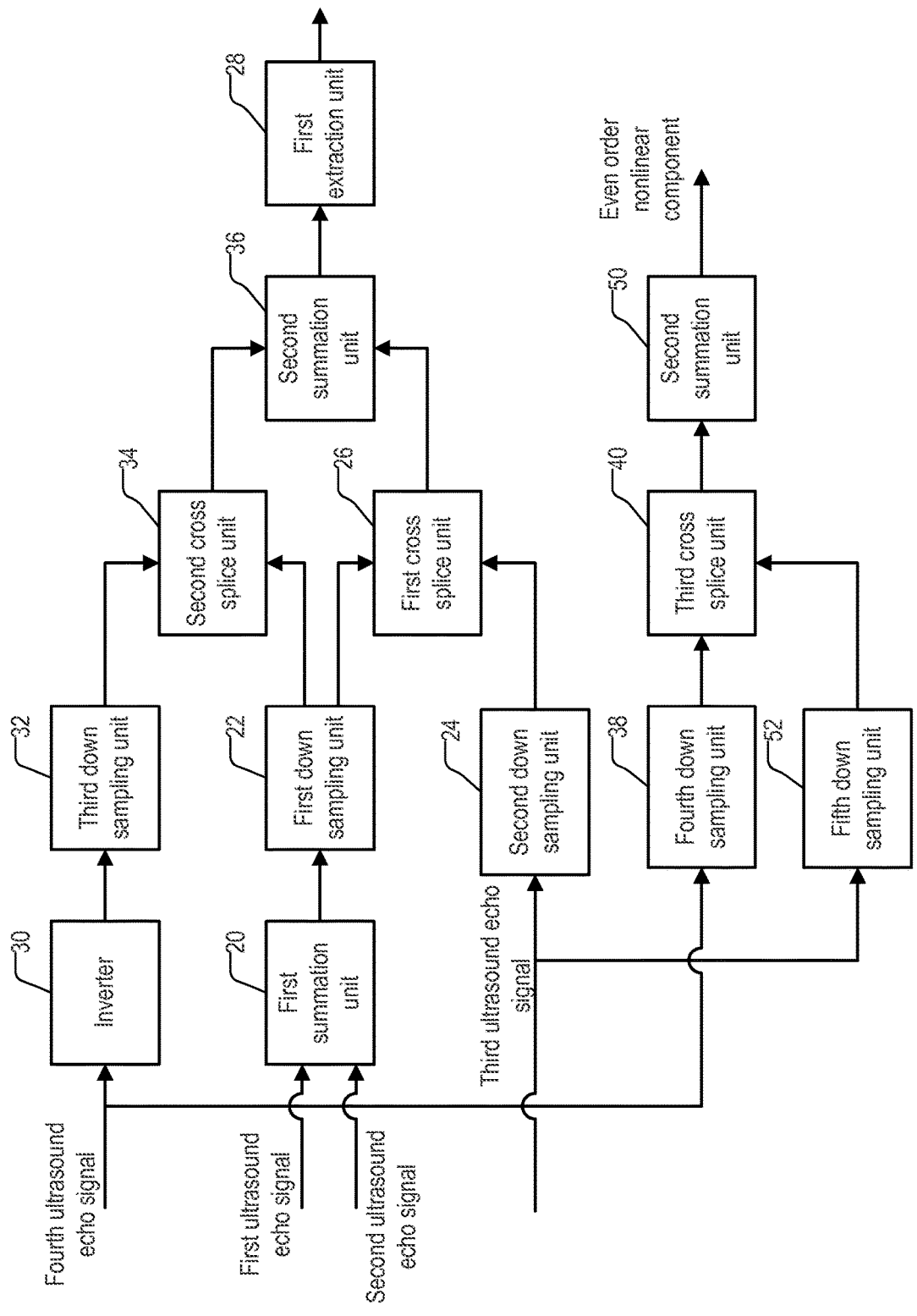
FIG. 12 is a block diagram of a signal process device according to still another embodiment of the present disclosure.

In these embodiments, the down-sampled third ultrasound echo signal obtained by down-sampling the third ultrasound echo signal which has been delayed by one point using the second down-sampling unit 24 is used. In other embodiments of the present disclosure, down-sampling the third ultrasound echo signal may not be performed by the second down-sampling unit 24, but by an additional fifth down-sampling unit 52, as shown in FIG. 12. In this case, it is possible that the fifth down-sampling unit 52 down-samples the third ultrasound echo signal, while the fourth down-sampling unit 38 down-samples the fourth ultrasound echo signal after delaying it by one point; or the fourth down-sampling unit 38 down-samples the fourth ultrasound echo signal, while the fifth down-sampling unit 52 down-samples the third ultrasound echo signal after delaying it by one point. The obtained down-sampled third ultrasound echo signal and down-sampled fourth ultrasound echo signal may be cross-combined by the third cross-combine unit 40 to obtain the fifth operation signal. Then, the secondary nonlinear component may be extracted from the fifth operation signal by the second extraction unit 50.

The configuration of other modules and other methods in these embodiments may be the same as or similar to those of the embodiments described above and will not be described in detail.

Figure 13:
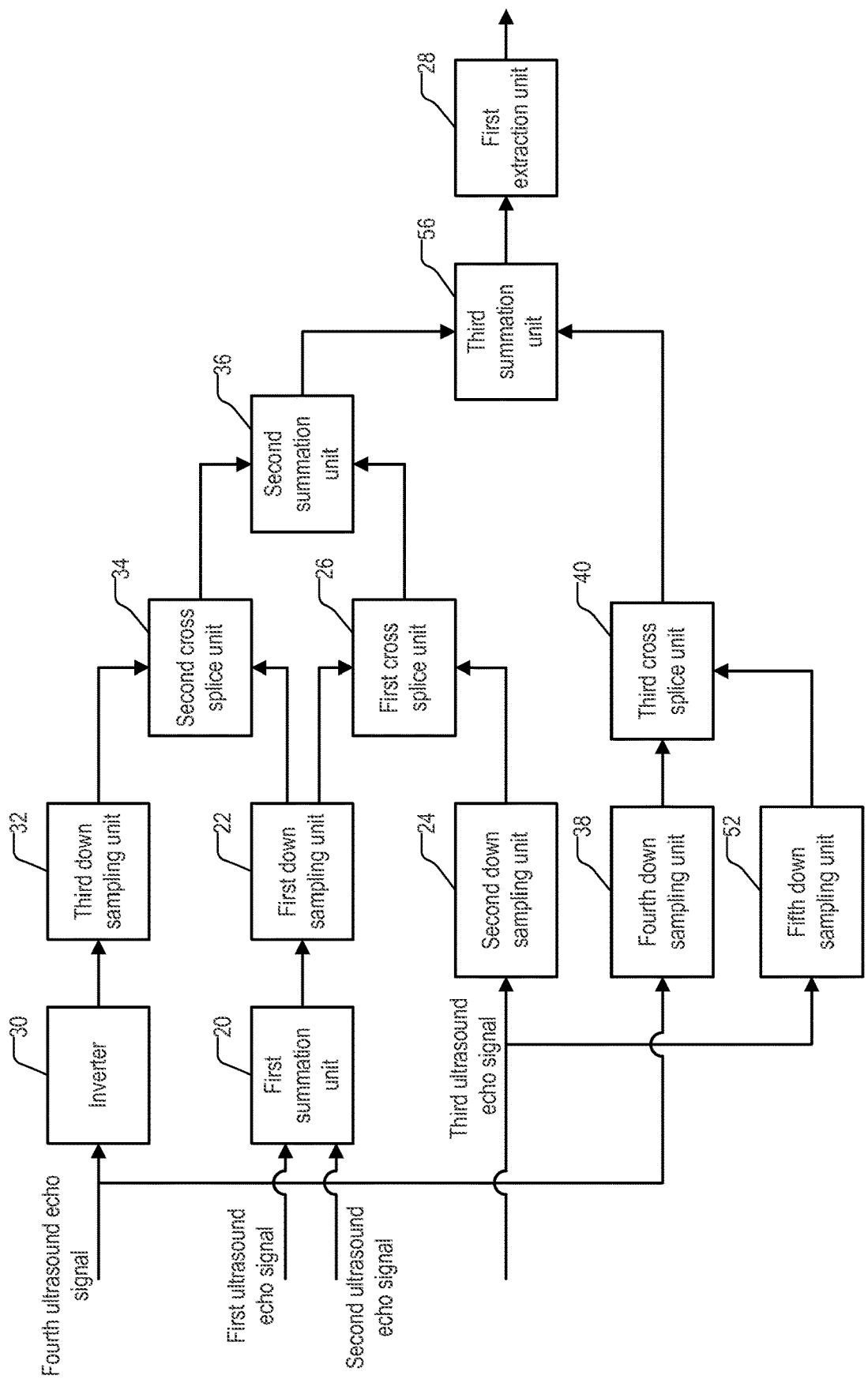
FIG. 13 is a block diagram of a signal process device according to still another embodiment of the present disclosure.

As shown in FIG. 13, in one embodiment of the present disclosure, other than being processed by a respective extraction unit to obtain needed signal components, the fourth operation signal and the fifth operation signal may be input into a third summation unit 56, which may sum the fourth operation signal and the fifth operation signal to obtain a sixth operation signal. Then the first extraction unit 28 may extract needed signal components from the sixth operation signal.

Figure 14:
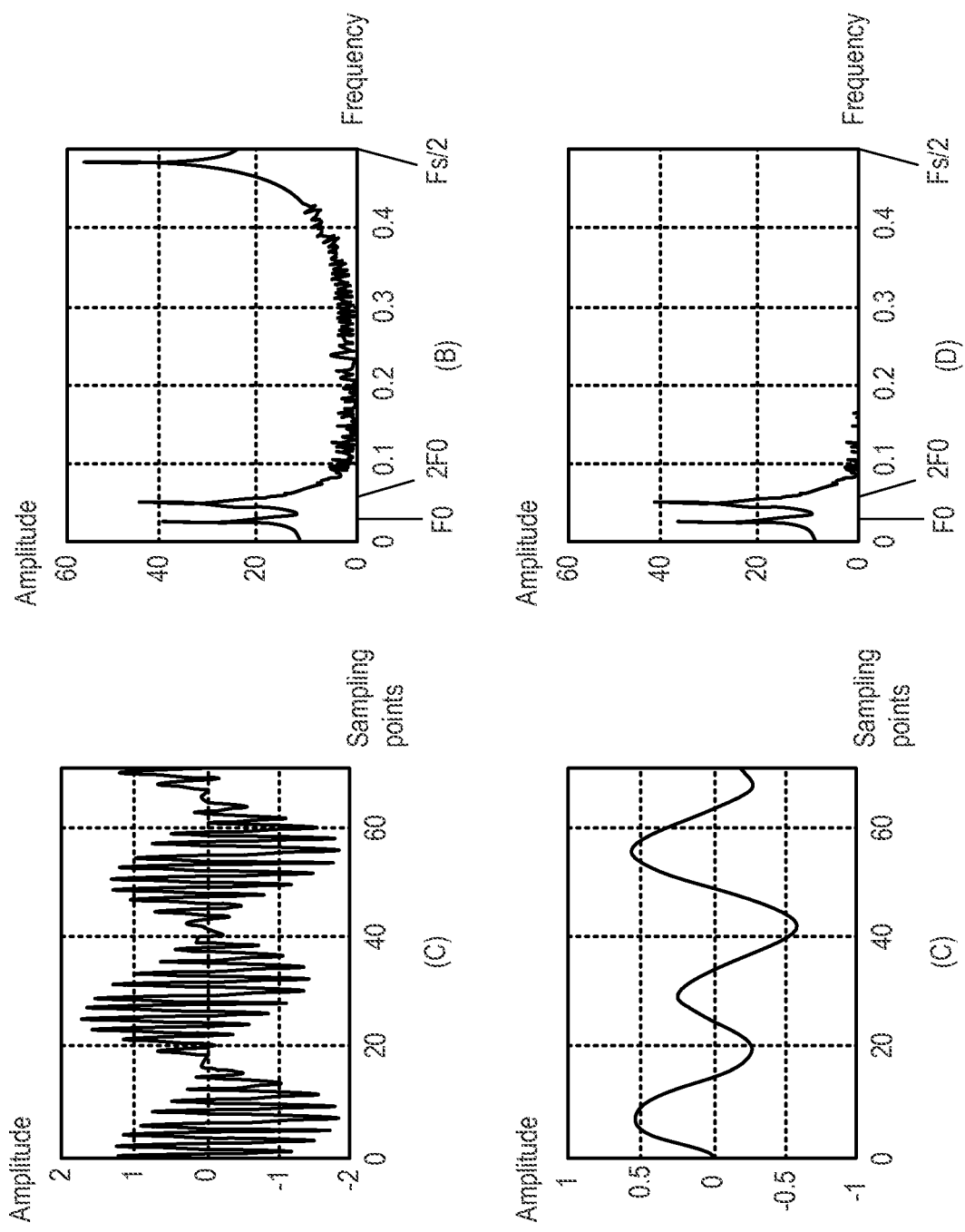
FIG. 14 is a group of schematics showing time domain waveforms and spectrums of a sixth operation signal according to an embodiment of the present disclosure.

As shown in FIG. 14, (A) is a schematic showing the time domain waveform of the sixth operation signal according to an embodiment, and (B) is a schematic showing the spectrum of the sixth operation signal shown in (B). It is shown that the sixth operation signal may contain a linear fundamental component, a nonlinear fundamental component and a secondary nonlinear component. The spectrum in (B) shows that, in a/the frequency domain, the asymmetrical component of the nonlinear fundamental component is located at the frequency position F0, the secondary nonlinear component is located at the frequency position 2F0, and the symmetrical component of the nonlinear fundamental component as well as the linear fundamental component are modulated to the frequency position Fs/2±F0.

Therefore, here, broadband detection may be used. For example, the secondary nonlinear component and the asymmetrical component of the nonlinear fundamental component may be extracted simultaneously by low-pass filtering. In FIG. 14, (C) is schematic showing the time domain waveform of the sixth operation signal which has been low-pass filtered, and (D) is a schematic showing the spectrum thereof.

In the embodiments of the present disclosure, by processing the echoes corresponding to a plurality of ultrasound pulses with different amplitudes and phases (or polarities) and modulating the echo signals, the linear component and the symmetrical components of the odd-order nonlinear components in the modulated signals may be shifted away from their original frequency position, while the even-order nonlinear components (for example, the secondary nonlinear component) and the asymmetrical components of the odd-order nonlinear components, particularly the nonlinear fundamental components generated by the three-order and higher odd-order components of the contrast agent echoes, may remain at their original frequency positions. Therefore, the separation of the even-order nonlinear components and the asymmetrical components of the odd-order nonlinear components from the linear components and the symmetrical components of the odd-order nonlinear components may be achieved without transmitting the plurality of ultrasound pulses in a way that the transmissions are delayed with respect to each other, and the even-order nonlinear components and/or the asymmetrical components of the odd-order nonlinear components may be easily extracted from the ultrasound echo signals for subsequent imaging processes, such as contrast agent imaging. Furthermore, according to the embodiments of the present disclosure, the linear components and the symmetrical components of the odd-order nonlinear components may be separated from the even-order nonlinear components and the asymmetrical components of the odd-order nonlinear components without transmitting the plurality of ultrasound pulses in a way that the transmissions are delayed with respect to each other, therefore the control processes for controlling the plurality of ultrasound pulses to be transmitted in a way that the transmissions are delayed with respect to each other may be avoided.

Although the present disclosure has been described through specific embodiments, it is not limited to these specific embodiments. Those of skill in the art should understand that various modifications, alternatives, and variations may be made based on the present disclosure, which should be in the scope of protection of the present disclosure. Furthermore, "a (an) embodiment" or "another embodiment" mentioned above may represent different embodiments, or may also be combined completely or partly in one embodiment.

What is claimed is:

1. A method for ultrasound imaging of a region of interest in a body using an ultrasound imaging system, the method comprising:
transmitting, via an ultrasound probe, a first amplitude weighted ultrasound pulse into the region of interest of the body;
receiving, via a receiving circuit, ultrasound echoes of the first ultrasound pulse reflected from the region of interest to obtain a first ultrasound echo signal;
transmitting, via the ultrasound probe, a second amplitude weighted ultrasound pulse to the region of interest;
receiving, via a receiving circuit, ultrasound echoes of the second ultrasound pulse reflected from the region of interest to obtain a second ultrasound echo signal;
transmitting, via the ultrasound probe, a third amplitude weighted ultrasound pulse to the region of interest;
receiving, via a receiving circuit, ultrasound echoes of the third ultrasound pulse reflected from the region of interest to obtain a third ultrasound echo signal;
processing the ultrasound echo signals using a signal processor by:
summing the first ultrasound echo signal with the second ultrasound echo signal to obtain a first operation signal;
inserting the third ultrasound echo signal into the first operation signal to obtain a second operation signal;
extracting at least one selected nonlinear echo signal component from the second operation signal; and
generating on a display an ultrasound image of the region of interest based on the at least one selected nonlinear echo signal component;
wherein amplitude weighting of the third ultrasound pulse is equal in magnitude to a sum of amplitude weightings of the first ultrasound pulse and the second ultrasound pulse.

2. The method of claim 1, wherein:
the amplitude weighting of the third ultrasound pulse is in the opposite direction of the sum of amplitude weightings of the first ultrasound pulse and the second ultrasound pulse.

3. The method of claim 2, wherein inserting the third ultrasound echo signal into the first operation signal to obtain a second operation signal comprises:
down-sampling the third ultrasound echo signal to obtain a down-sampled third ultrasound echo signal;
down-sampling the first operation signal to obtain a down-sampled first operation signal; and
inserting the down-sampled third ultrasound echo signal into the down-sampled first operation signal to obtain the second operation signal.

4. The method of claim 3, further comprising:
before down-sampling the third ultrasound echo signal, summing each data point in the third ultrasound echo signal with at least one adjacent data point in said third ultrasound echo signal, and replacing said data point with the sum; and/or
before down-sampling the first operation signal, summing each data point in the first operation signal with at least one adjacent data point in said first operation signal, and replacing said data point with the sum.

5. The method of claim 1, further comprising:
transmitting a fourth ultrasound pulse to the region of interest;
receiving ultrasound echoes of the fourth ultrasound pulse reflected from the region of interest to obtain a fourth ultrasound echo signal;
wherein:
the amplitude weighting of the third ultrasound pulse is in the opposite direction of the sum of amplitude weightings of the first ultrasound pulse and the second ultrasound pulse;
amplitude weighting of the fourth ultrasound pulse and the sum of amplitude weightings of the first ultrasound pulse and the second ultrasound pulse have same magnitude and direction; and
extracting the at least one selected nonlinear echo signal component from the second operation signal comprises:
extracting at least one selected nonlinear echo signal component based on the first ultrasound echo signal, the second ultrasound echo signal, the third ultrasound echo signal and the fourth ultrasound echo signal.

6. The method of claim 5, wherein extracting the at least one selected nonlinear echo signal component based on the first ultrasound echo signal, the second ultrasound echo signal, the third ultrasound echo signal and the fourth ultrasound echo signal comprises:
inverting the fourth ultrasound echo signal and inserting the inverted fourth ultrasound echo signal and the first operation signal to obtain a third operation signal;
summing the second operation signal with the third operation signal to obtain a fourth operation signal; and
extracting the at least one selected nonlinear echo signal component from the fourth operation signal.

7. The method of claim 6, wherein inserting the third ultrasound echo signal and the first operation signal to obtain a second operation signal and inverting the fourth ultrasound echo signal and inserting the inverted fourth ultrasound echo signal and the first operation signal to obtain a third operation signal comprises:
down-sampling the first operation signal to obtain a down-sampled first operation signal;
down-sampling the third ultrasound echo signal to obtain a down-sampled third ultrasound echo signal;
inverting the fourth ultrasound echo signal to obtain an inverted fourth ultrasound echo signal;
down-sampling the inverted fourth ultrasound echo signal to obtain a down-sampled, inverted fourth ultrasound echo signal;
inserting the down-sampled third ultrasound echo signal and the down-sampled first operation signal to obtain the second operation signal; and
inserting the down-sampled, inverted fourth ultrasound echo signal and the down-sampled first operation signal to obtain the third operation signal.

8. The method of claim 7, further comprising:
before down-sampling the first operation signal,
summing each data point in the first operation signal with at least one adjacent data point in said first operation signal, and replacing said data point with the sum; and/or
before down-sampling the third ultrasound echo signal,
summing each data point in the third ultrasound echo signal with at least one adjacent data point in said third ultrasound echo signal, and replacing said data point with the sum; and/or
before down-sampling the fourth inverted ultrasound echo signal,
summing each data point in the inverted fourth ultrasound echo signal with at least one adjacent data point in said inverted fourth ultrasound echo signal, and replacing said data point with the sum.

9. The method of claim 5, further comprising:
inserting the third ultrasound echo signal and the fourth ultrasound echo signal to obtain a fifth operation signal;
extracting an even-order nonlinear component from the fifth operation signal; and
generating an ultrasound image of the region of interest based on the even-order nonlinear component.

10. The method of claim 9, wherein
inserting the third ultrasound echo signal and the fourth ultrasound echo signal to obtain a fifth operation signal comprises:
down-sampling the third ultrasound echo signal to obtain a down-sampled third ultrasound echo signal;
down-sampling the fourth ultrasound echo signal to obtain a down-sampled fourth ultrasound echo signal;
inserting the third down-sampled ultrasound signal and the down-sampled fourth ultrasound echo signal to obtain the fifth operation signal.

11. The method of claim 10, further comprising:
before down-sampling the third ultrasound echo signal, summing each data point in the third ultrasound echo signal with at least one adjacent data point in said third ultrasound echo signal, and replacing said data point with the sum; and/or
before down-sampling the fourth ultrasound echo signal, summing each data point in the fourth ultrasound echo signal with at least one adjacent data point in said fourth ultrasound echo signal, and replacing said data point with the sum.

12. The method of claim 9, further comprising:
summing the fourth operation signal and the fifth operation signal to obtain a sixth operation signal; and
extracting at least one selected nonlinear echo signal component from the sixth operation signal.

13. The method of claim 1, wherein:
the amplitude weighting of the third ultrasound pulse is in the same direction as the sum of amplitude weightings of the first ultrasound pulse and the second ultrasound pulse; and
inverting the third ultrasound echo signal and inserting the inverted third ultrasound echo signal into the first operation signal to obtain the second operation signal.

14. The method of claim 13, wherein inverting the third ultrasound echo signal and inserting the inverted third ultrasound echo signal into the first operation signal to obtain a second operation signal comprises:
inverting the third ultrasound echo signal to obtain an inverted third ultrasound echo signal;
down-sampling the inverted third ultrasound echo signal to obtain a down-sampled, inverted third ultrasound echo signal;
down-sampling the first operation signal to obtain a down-sampled first operation signal; and
inserting the down-sampled, inverted third ultrasound echo signal into the down-sampled first operation signal to obtain the second operation signal.

15. The method of claim 14, further comprising:
before down-sampling the third inverted ultrasound echo signal,
summing each data point in the inverted third ultrasound echo signal with at least one adjacent data point in said inverted third ultrasound echo signal, and replacing said data point with the sum; and/or
before down-sampling the first operation signal, summing each data point in the first operation signal with at least one adjacent data point in said first operation signal, and replacing said data point with the sum.

16. The method of claim 1, wherein the at least one selected nonlinear echo signal component comprises an asymmetrical component of a nonlinear fundamental component and/or an even-order nonlinear component.

17. An ultrasound imaging system for imaging a region of interest in a body, comprising:
a probe;
a transmitting circuit configured to transmit a first amplitude weighted ultrasound pulse, a second amplitude weighted ultrasound pulse and a third amplitude weighted ultrasound pulse to the region of interest through the probe;
a receiving circuit configured to, through the probe, respectively receive ultrasound echoes of the first ultrasound pulse to obtain a first ultrasound echo signal, receive ultrasound echoes of the second ultrasound pulse to obtain a second ultrasound echo signal and receive ultrasound echoes of the third ultrasound pulse to obtain a third ultrasound echo signal;
a signal processor configured to extract an echo signal component based on the first ultrasound echo signal, the second ultrasound echo signal and the third ultrasound echo signal, said signal processor configured to:
sum the first ultrasound echo signal with the second ultrasound echo signal to obtain a first operation signal;
insert the third ultrasound echo signal into the first operation signal to obtain a second operation signal; and
extract at least one selected nonlinear echo signal component from the second operation signal; and
an image processor configured to generate an image of the region of interest based on the selected nonlinear echo signal component;
wherein amplitude weighting of the third ultrasound pulse is equal in magnitude to a sum of amplitude weightings of the first ultrasound pulse and the second ultrasound pulse.

18. The system of claim 17, wherein:
the amplitude weighting of the third ultrasound pulse is in an opposite direction of the sum of amplitude weightings of the first ultrasound pulse and the second ultrasound pulse.

19. The system of claim 18, wherein the signal processor is further configured to:
down-sample the first operation signal to obtain a down-sampled first operation signal;
down-sample the third ultrasound echo signal to obtain a down-sampled third ultrasound echo signal;
insert the down-sampled third ultrasound echo signal into the down-sampled first operation signal to obtain the second operation signal.

20. The system of claim 17, wherein:
the transmitting circuit is further configured to transmit a fourth ultrasound pulse to the region of interest through the probe;
the receiving circuit is further configured to receive ultrasound echoes of the fourth ultrasound pulse through the probe to obtain a fourth ultrasound echo signal;
wherein:
the amplitude weighting of the third ultrasound pulse is in the opposite direction of the sum of amplitude weightings of the first ultrasound pulse and the second ultrasound pulse;
the amplitude weighting of the fourth ultrasound pulse and the sum of amplitude weightings of the first ultrasound pulse and the second ultrasound pulse have the same magnitudes and directions; and the signal processor modulo is further configured to extract the at least one selected nonlinear echo signal component based on the first ultrasound echo signal, the second ultrasound echo signal, the third ultrasound echo signal and the fourth ultrasound echo signal.

21. The system of claim 20, wherein the signal processor is further configured to:
sum the first ultrasound echo signal with the second ultrasound echo signal to obtain a first operation signal;
insert the third ultrasound echo signal and the first operation signal to obtain a second operation signal;
invert the fourth ultrasound echo signal;
insert the inverted fourth ultrasound echo signal and the first operation signal to obtain a third operation signal;
sums the second operation signal with the third operation signal to obtain a fourth operation signal; and
extracts the at least one selected nonlinear echo signal component from the fourth operation signal.

22. The system of claim 21, wherein the signal process unit is further configured to:
down-sample the first operation signal to obtain a down-sampled first operation signal;
down-sample the third ultrasound echo signal to obtain a down-sampled third ultrasound echo signal; and
down-sample the inverted fourth ultrasound echo signal to obtain a down-sampled, inverted fourth ultrasound echo signal;
insert the down-sampled third ultrasound echo signal and the down-sampled first operation signal to obtain the second operation signal; and
insert the down-sampled, inverted fourth ultrasound echo signal and the down-sampled first operation signal to obtain the third operation signal.

23. The system of claim 20, wherein the signal processing module is further configured to:
insert the third ultrasound echo signal and the fourth ultrasound echo signal to obtain a fifth operation signal; and
extract an even-order nonlinear component from the fifth operation signal;
wherein the image processing module is further configured to generate the ultrasound image of the region of interest based on the even-order nonlinear component.

24. The system of claim 23, wherein the signal processing module is further configured to:
down-sample the third ultrasound echo signal to obtain a down-sampled third ultrasound echo signal; and
down-sample the fourth ultrasound echo signal to obtain a down-sampled fourth ultrasound echo signal; and
cross combine insert the third down-sampled ultrasound signal and the down-sampled fourth ultrasound echo signal to obtain the fifth operation signal.

25. The system of claim 20, wherein the signal processing module is further configured to:
insert the third ultrasound echo signal and the fourth ultrasound echo signal to obtain a fifth operation signal; and
sum the fourth operation signal and the fifth operation signal to obtain a sixth operation signal; and
extract the at least one selected nonlinear echo signal component from the sixth operation signal.

26. The system of claim 25, wherein the signal processing module is further configured to:
down-sample the fourth ultrasound echo signal to obtain a down-sampled fourth ultrasound echo signal;
down-sample the third ultrasound echo signal to obtain a down-sampled third ultrasound echo signal; and
insert the down-sampled third ultrasound echo signal and the down-sampled fourth ultrasound echo signal to obtain a fifth operation signal.

27. The system of claim 17, wherein:
the amplitude weighting of the third ultrasound pulse is in the same direction as the sum of the amplitude weightings of the first ultrasound pulse and the second ultrasound pulse;
wherein the signal processor further comprises:
an inverter configured to invert the third ultrasound echo signal.

28. The system of claim 27, wherein the signal processor is further configured to:
down-sample the first operation signal to obtain a down-sampled first operation signal; and
down-sample the inverted third ultrasound echo signal to obtain a down-sampled, inverted third ultrasound echo signal; and
insert the down-sampled, inverted third ultrasound echo signal into the down-sampled first operation signal to obtain the second operation signal.

29. The system of claim 17, wherein the selected nonlinear echo signal component comprises an asymmetrical component of a nonlinear fundamental component and/or an even-order nonlinear component.

* * * * *